(12) United States Patent
Buesing et al.

(10) Patent No.: US 8,993,123 B2
(45) Date of Patent: Mar. 31, 2015

(54) MATERIALS FOR ORGANIC ELECTROLUMINESCENT DEVICES

(75) Inventors: Arne Buesing, Frankfurt (DE); Holger Heil, Darmstadt (DE); Philipp Stoessel, Frankfurt am Main (DE)

(73) Assignee: Merck Patent GmbH (DE)

( * ) Notice: Subject to any disclaimer, the term of this patent is extended or adjusted under 35 U.S.C. 154(b) by 83 days.

(21) Appl. No.: 12/867,648

(22) PCT Filed: Feb. 13, 2009

(86) PCT No.: PCT/EP2009/001028
§ 371 (c)(1),
(2), (4) Date: Aug. 13, 2010

(87) PCT Pub. No.: WO2009/100925
PCT Pub. Date: Aug. 20, 2009

(65) Prior Publication Data
US 2010/0327270 A1    Dec. 30, 2010

(30) Foreign Application Priority Data
Feb. 13, 2008   (DE) .......................... 10 2008 008 953

(51) Int. Cl.
| | |
|---|---|
| *H01L 51/54* | (2006.01) |
| *H01L 51/00* | (2006.01) |
| *C07C 13/567* | (2006.01) |
| *C07C 13/72* | (2006.01) |
| *C07C 15/20* | (2006.01) |
| *C07C 15/30* | (2006.01) |
| *C07C 15/38* | (2006.01) |
| *C07C 211/54* | (2006.01) |
| *C07C 211/61* | (2006.01) |
| *C07D 221/10* | (2006.01) |
| *C07D 235/18* | (2006.01) |
| *C07D 251/24* | (2006.01) |
| *C07D 333/08* | (2006.01) |
| *C07D 333/72* | (2006.01) |
| *C07D 471/04* | (2006.01) |
| *C09K 11/06* | (2006.01) |
| *H05B 33/14* | (2006.01) |
| *H01L 51/50* | (2006.01) |

(52) U.S. Cl.
CPC .......... *H01L 51/0058* (2013.01); *C07C 13/567* (2013.01); *C07C 13/72* (2013.01); *C07C 15/20* (2013.01); *C07C 15/30* (2013.01); *C07C 15/38* (2013.01); *C07C 211/54* (2013.01); *C07C 211/61* (2013.01); *C07D 221/10* (2013.01); *C07D 235/18* (2013.01); *C07D 251/24* (2013.01); *C07D 333/08* (2013.01); *C07D 333/72* (2013.01); *C07D 471/04* (2013.01); *C09K 11/06* (2013.01); *H05B 33/14* (2013.01); C07C 2101/14 (2013.01); C07C 2103/18 (2013.01); C07C 2103/24 (2013.01); C07C 2103/26 (2013.01); C07C 2103/42 (2013.01); C07C 2103/52 (2013.01); C07C 2103/94 (2013.01); C09K 2211/1014 (2013.01); C09K 2211/1044 (2013.01); C09K 2211/1059 (2013.01); H01L 51/006 (2013.01); H01L 51/0081 (2013.01); H01L 51/5048 (2013.01); Y02E 10/549 (2013.01); Y10S 428/917 (2013.01)
USPC ........... 428/690; 428/917; 313/504; 313/505; 313/506; 257/40; 257/E51.05; 257/E51.026; 257/E51.032; 257/E51.052; 548/304.1; 548/418; 548/440; 548/444; 585/27

(58) Field of Classification Search
USPC .................. 428/690, 917; 313/504, 505, 506; 257/40, E51.05, E51.026, E51.032, 257/E51.052; 548/304.1, 418, 440, 444; 585/27
See application file for complete search history.

(56) References Cited

U.S. PATENT DOCUMENTS

| | | |
|---|---|---|
| 4,539,507 A | 9/1985 | VanSlyke et al. |
| 5,151,629 A | 9/1992 | VanSlyke |
| 5,840,217 A | 11/1998 | Lupo et al. |
| 5,935,721 A | 8/1999 | Shi et al. |
| 6,458,909 B1 | 10/2002 | Spreitzer et al. |
| 6,534,199 B1 | 3/2003 | Hosokawa et al. |
| 6,713,192 B2 | 3/2004 | Fukuoka et al. |
| 7,365,198 B2 | 4/2008 | Saitoh et al. |
| 7,701,131 B2 | 4/2010 | Gerhard et al. |
| 2005/0089717 A1* | 4/2005 | Cosimbescu et al. ......... 428/690 |
| 2005/0214565 A1 | 9/2005 | Ikeda et al. |
| 2005/0233165 A1 | 10/2005 | Ido et al. |
| 2006/0043858 A1 | 3/2006 | Ikeda et al. |
| 2006/0063027 A1 | 3/2006 | Vestweber et al. |

(Continued)

FOREIGN PATENT DOCUMENTS

| | | |
|---|---|---|
| CN | 1362464 | 8/2002 |
| CN | 101595575 A | 12/2009 |

(Continued)

OTHER PUBLICATIONS

Hassan et al., Aryl-Aryl Bond Formation One Century after the Discovery of the Ullmann Reaction, 2002, Chemical Reviews, vol. 102, pp. 1359-1469.*

(Continued)

*Primary Examiner* — Gregory Clark
(74) *Attorney, Agent, or Firm* — Drinker Biddle & Reath LLP

(57) ABSTRACT

The present invention relates to the compounds of the formula (1) and to organic electroluminescent devices, in particular blue-emitting devices, in which these compounds are used as host material in the emitting layer and/or as electron-transport material.

17 Claims, No Drawings

(56) References Cited

U.S. PATENT DOCUMENTS

| | | | |
|---|---|---|---|
| 2007/0037983 A1 | 2/2007 | Nomura et al. | |
| 2007/0247063 A1 | 10/2007 | Murase et al. | |
| 2008/0004445 A1 | 1/2008 | Hosokawa et al. | |
| 2008/0079356 A1 | 4/2008 | Park et al. | |
| 2008/0093980 A1 | 4/2008 | Stoessel et al. | |
| 2008/0125609 A1 | 5/2008 | Vestweber et al. | |
| 2008/0145698 A1 | 6/2008 | Heil et al. | |
| 2008/0182129 A1* | 7/2008 | Klubek et al. | 428/704 |
| 2008/0220285 A1 | 9/2008 | Vestweber et al. | |
| 2008/0272693 A1 | 11/2008 | Heil et al. | |
| 2009/0009073 A1 | 1/2009 | Ikeda et al. | |
| 2009/0159874 A1 | 6/2009 | Vestweber et al. | |
| 2009/0184313 A1 | 7/2009 | Buesing et al. | |
| 2009/0261717 A1 | 10/2009 | Buesing et al. | |
| 2010/0320452 A1 | 12/2010 | Kawamura | |

FOREIGN PATENT DOCUMENTS

| | | |
|---|---|---|
| EP | 676461 | 10/1995 |
| JP | 2001-332384 | 11/2001 |
| JP | 2005041843 A | 2/2005 |
| JP | 2007230951 A | 9/2007 |
| WO | WO-9827136 | 6/1998 |
| WO | WO-01/21729 | 3/2001 |
| WO | WO-01/76323 | 10/2001 |
| WO | WO-03/087023 | 10/2003 |
| WO | WO-03/095445 | 11/2003 |
| WO | WO-2004/013073 | 2/2004 |
| WO | WO-2004/016575 | 2/2004 |
| WO | WO-2004/018587 | 3/2004 |
| WO | WO-2004/018588 | 3/2004 |
| WO | WO-2004/058911 | 7/2004 |
| WO | WO-2005/011013 | 2/2005 |
| WO | WO-2005113531 A1 | 12/2005 |
| WO | WO-2006/000388 | 1/2006 |
| WO | WO-2006/000389 | 1/2006 |
| WO | WO-2006005626 A2 | 1/2006 |
| WO | WO-2006/058737 | 6/2006 |
| WO | WO-2006/122630 | 11/2006 |
| WO | WO-2007/005610 | 1/2007 |
| WO | WO-2007/065549 | 6/2007 |
| WO | WO-2007/123256 | 11/2007 |
| WO | WO-2007/140847 | 12/2007 |
| WO | WO-2008/006449 | 1/2008 |
| WO | WO-2008/094399 | 8/2008 |
| WO | WO-2008/094399 A1 | 8/2008 |
| WO | WO-2009/069566 A1 | 6/2009 |

OTHER PUBLICATIONS

Schmittel, M., et al., "Synthesis of Sterically Encumbered 2,9-Diaryl Substituted Phenanthrolines, Key Building Blocks for the Preparation of Mixed (Bis-Heteroleptic) Phenanthroline Copper(I) Complexes(I)", Heterocyclic Communications, vol. 3, No. 6, (1997), pp. 493-498.

Schmittel, M., et al., "New Sterically Encumbered 2,9-Diarylphenanthrolines for the Selective Formation of Heteroleptic Bis(phenanthroline) copper(I) Complexes", European Journal of Inorganic Chemistry, vol. 5, (2001), pp. 1155-1166.

English Translation of ISR in PCT/EP2009/001028, mailed Jun. 25, 2009.

English Translation of IPRP in PCT/EP2009/001028, mailed Sep. 7, 2010.

* cited by examiner

MATERIALS FOR ORGANIC ELECTROLUMINESCENT DEVICES

CROSS-REFERENCE TO RELATED APPLICATIONS

This application is a national stage application (under 35 U.S.C. §371) of PCT/EP2009/001028, filed Feb. 13, 2009, which claims benefit of German application 10 2008 008 953.2, filed Feb. 13, 2008.

BACKGROUND OF THE INVENTION

The present invention relates to organic semiconductors and to the use thereof in organic electronic devices.

Organic semiconductors are being developed for a number of electronic applications of different types. The structure of organic electroluminescent devices (OLEDs) in which these organic semiconductors are employed as functional materials is described, for example, in U.S. Pat. No. 4,539,507, U.S. Pat. No. 5,151,629, EP 0676461 and WO 98/27136. However, further improvements are still necessary before these devices can be used for high-quality and long-lived displays. Thus, in particular, the lifetime and the efficiency of deep-blue-emitting organic electroluminescent devices currently still represent a problem for which there is still a need for improvement. Furthermore, it is necessary for the compounds to have high thermal stability and a high glass-transition temperature and to be sublimable without decomposition. In particular for use at elevated temperature, a high glass-transition temperature is essential in order to achieve long lifetimes.

For fluorescent OLEDs, principally condensed aromatic compounds, in particular anthracene derivatives, are used in accordance with the prior art as host materials, especially for blue-emitting electroluminescent devices, for example 9,10-bis(2-naphthyl)anthracene (U.S. Pat. No. 5,935,721). WO 03/095445 and CN 1362464 disclose 9,10-bis(1-naphthyl) anthracene derivatives for use in OLEDs. Further anthracene derivatives are disclosed in WO 01/076323, in WO 01/021729, in WO 04/013073, in WO 04/018588, in WO 03/087023 or in WO 04/018587. Host materials based on aryl-substituted pyrenes and chrysenes are disclosed in WO 04/016575. For high-quality applications, it is necessary to have improved host materials available.

Thus, there continues to be a demand for improved materials, in particular host materials for fluorescent emitters, especially for blue-fluorescent emitters, which result in good efficiencies and at the same time in long lifetimes in organic electronic devices, lead to reproducible results during production and operation of the device, have a high glass-transition temperature and can be sublimed without decomposition. Further improvements are also necessary in electron-transport materials.

Surprisingly, it has been found that anthracene derivatives which are substituted in the 9-position by a 3-phenanthrenyl group, where both the anthracene and also the phenanthrene may be further substituted, exhibit significant improvements here and are very highly suitable for use in organic electroluminescent devices. These compounds enable an increase in the efficiency and especially in the lifetime of the organic electronic device to be achieved compared with materials in accordance with the prior art. This applies, in particular, to deep-blue-fluorescent devices. Furthermore, these compounds have high thermal stability. In general, these materials are very highly suitable for use in organic electronic devices since they have a high glass-transition temperature. The present invention therefore relates to these materials and to the use thereof in organic electronic devices.

For reasons of clarity, the numbering of the positions of anthracene and phenanthcene is shown below:

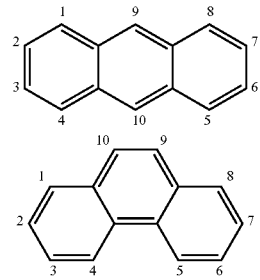

JP 2001/332384 claims organic electroluminescent devices which contain phenanthrene derivatives, where the phenanthrene may also be substituted by aromatic groups besides other substituents. However, JP 2001/332384 does not teach that in particular an anthracene to which a 3-phenanthrenyl group is bonded in the 9-position achieves particularly good results in organic electroluminescent devices.

WO 07/123,256 claims in general fluoranthene-9-anthracene compounds for use in organic electroluminescent devices. The anthracene here may also be substituted in the 10-position by further aromatic groups. Besides a large number of other aromatic groups, two structures which contain a 3-phenanthrenyl group on the anthracene in the 10-position are also mentioned. However, the inventive effect of these compounds is attributed to the combination of the fluoranthene unit with the 9-anthracene unit. The presence of the phenanthrenyl group is not accorded any importance.

BRIEF SUMMARY OF THE INVENTION

The invention relates to compounds of the formula (1)

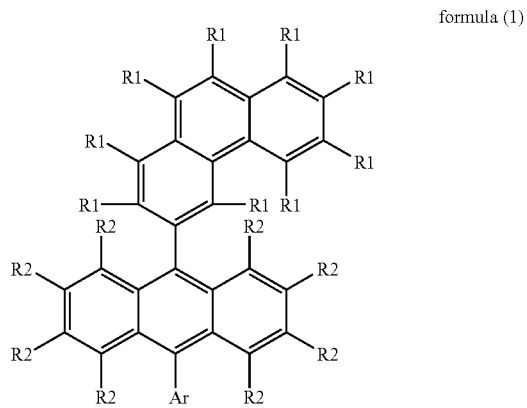

formula (1)

where a C—R1 group in the phenanthrene unit may also be replaced by N, where one or more C—R2 groups in the anthracene unit may also be replaced by N, and where the following applies to the symbols used:

Ar is H, D or an aromatic or heteroaromatic ring system having 5 to 60 aromatic ring atoms, which may be substituted by one or more non-aromatic radicals R1;

R1 is, identically or differently on each occurrence, H, D, F, Cl, Br, I, CHO, N(Ar1)$_2$, C(=O)Ar1, P(Ar1)$_2$, P(=O)

(Ar1)$_2$, S(=O)Ar1, S(=O)$_2$Ar1, CR3=CR3Ar1, CN, NO$_2$, Si(R3)$_3$, B(OAr1)$_2$, B(OR3)$_2$, OSO$_2$R3, OH, a straight-chain alkyl, alkoxy or thioalkoxy group having 1 to 40 C atoms or a branched or cyclic alkyl, alkoxy or thioalkoxy group having 3 to 40 C atoms, which may each be substituted by one or more radicals R3, where one or more non-adjacent CH$_2$ groups may be replaced by R3C=CR3, C≡C, Si(R3)$_2$, Ge(R3)$_2$, Sn(R3)$_2$, C=O, C=S, C=Se, C=NR3, P(=O)(R3), SO, SO$_2$, NR3, O, S or CONR3 and where one or more H atoms may be replaced by F, Cl, Br, I, CN or NO$_2$, or an aromatic or heteroaromatic ring system having 5 to 60 aromatic ring atoms, which may each be substituted by one or more non-aromatic radicals R1, or an aryloxy or heteroaryloxy group having 5 to 60 aromatic ring atoms, which may be substituted by one or more non-aromatic radicals R1, or a combination of these systems;

R2 is, identically or differently on each occurrence, R1, or two or more adjacent substituents R2 form a mono- or polycyclic, aliphatic or aromatic ring system with one another;

Ar1 is, identically or differently on each occurrence, an aromatic or heteroaromatic ring system having 5 to 30 aromatic ring atoms, which may be substituted by one or more non-aromatic radicals R3; two radicals Ar1 which are bonded to the same nitrogen or phosphorus atom may also be linked to one another here by a single bond or a bridge selected from B(R3), C(R3)$_2$, Si(R3)$_2$, C=O, C=NR3, C=C(R3)$_2$, O, S, S=O, SO$_2$, N(R3), P(R3) and P(=O)R3;

R3 is on each occurrence, identically or differently, H or an aliphatic, aromatic and/or heteroaromatic hydrocarbon radical having 1 to 20 C atoms, in which, in addition, one or more H atoms may be replaced by F; two or more adjacent substituents R3 here may also form a mono- or polycyclic aliphatic or aromatic ring system with one another;

the following two compounds are excluded from the invention:

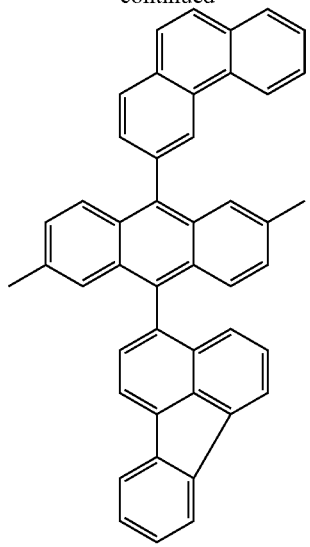

DETAILED DESCRIPTION OF THE INVENTION

The compounds of the formula (1) preferably have a glass-transition temperature $T_g$ of greater than 70° C., particularly preferably greater than 100° C., very particularly preferably greater than 120° C.

In a preferred embodiment of the invention, Ar does not represent a fluoranthene group and does not contain a fluoranthene group which is bonded directly to the anthracene.

For the purposes of this invention, an aryl group contains 6 to 60 C atoms; for the purposes of this invention, a heteroaryl group contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a single aromatic ring, i.e. benzene, or a single heteroaromatic ring, for example pyridine, pyrimidine, thiophene, etc., or a condensed aryl or heteroaryl group, for example naphthalene, anthracene, pyrene, quinoline, isoquinoline, benzimidazole, phenanthrene, etc.

For the purposes of this invention, an aromatic ring system contains 6 to 60 C atoms in the ring system. For the purposes of this invention, a heteroaromatic ring system contains 2 to 60 C atoms and at least one heteroatom in the ring system, with the proviso that the sum of C atoms and heteroatoms is at least 5. The heteroatoms are preferably selected from N, O and/or S. For the purposes of this invention, an aromatic or heteroarouratic ring system is intended to be taken to mean a system which does not necessarily contain only aryl or heteroaryl groups, but instead in which a plurality of aryl or heteroaryl groups may also be interrupted by a short non-aromatic unit (preferably less than 10% of the atoms other than H), such as, for example, an sp$^3$-hybridised C, N or O atom. Thus, for example, systems such as 9,9'-spirobifluorene, 9,9-diarylfluorene, cis- and trans-indenofluorene, benzindenofluorene, dibenzoindenofluorene, triarylamine, diaryl ether, stilbene, benzophenone, etc., are also intended to be taken to mean aromatic ring systems for the purposes of this invention. An aromatic or heteroaromatic ring system is likewise taken to mean systems in which a plurality of aryl or heteroaryl groups are linked to one another by single bonds, for example biphenyl, terphenyl or bipyridine.

For the purposes of the present invention, a $C_1$- to $C_{40}$-alkyl group, in which, in addition, individual H atoms or $CH_2$ groups may be substituted by the above-mentioned groups, is particularly preferably taken to mean the radicals methyl, ethyl, n-propyl, i-propyl, n-butyl, i-butyl, s-butyl, t-butyl, 2-methylbutyl, n-pentyl, s-pentyl, cyclopentyl, n-hexyl, cyclohexyl, n-heptyl, cycloheptyl, n-octyl, cyclooctyl, 2-ethylhexyl, trifluoromethyl, pentafluoro-ethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl. A $C_1$- to $C_{40}$-alkoxy group is particularly preferably taken to mean methoxy, trifluoro-methoxy, ethoxy, n-propoxy, i-propoxy, n-butoxy, i-butoxy, s-butoxy, t-butoxy or 2-methylbutoxy. An aromatic or heteroaromatic ring system having 5-60 aromatic ring atoms, which may also in each case be substituted by the above-mentioned radicals R and which can be linked to the aromatic or heteroaromatic ring system via any desired positions, is taken to mean, in particular, groups derived from benzene, naphthalene, anthracene, phenanthrene, pyrene, chrysene, perylene, fluoranthene, naphthacene, pentacene, benzanthracene, benzopyrene, biphenyl, biphenylene, terphenyl, terphenylene, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiopherie, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In a preferred embodiment of the invention, a maximum of one C—R2 group in the anthracene unit of the formula (1) is replaced by N. Particularly preferably, no C—R2 group is replaced by N, i.e. it is an anthracene and not a heterocycle. Again preferably, no C—R1 group in the phenanthrene unit is also replaced by N, i.e. it is a phenanthrene and not a heterocycle.

Preferred embodiments of the present invention are compounds of the formula (2) to formula (7):

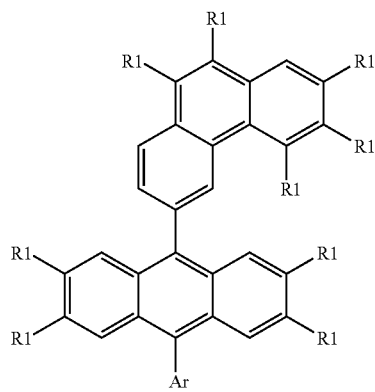

formula (2)

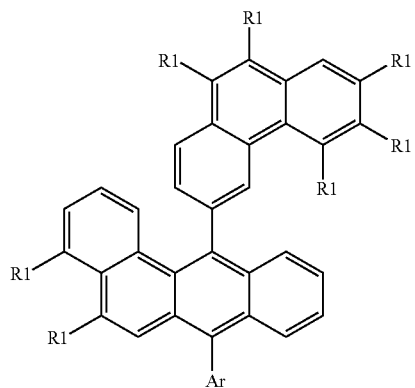

formula (3)

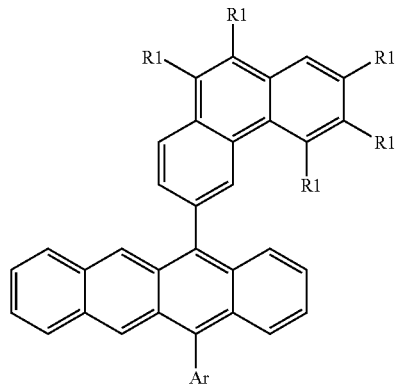

formula (4)

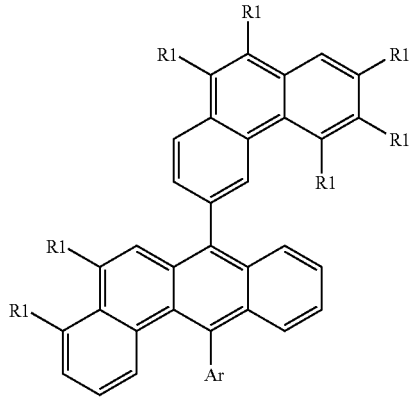

formula (5)

formula (6)

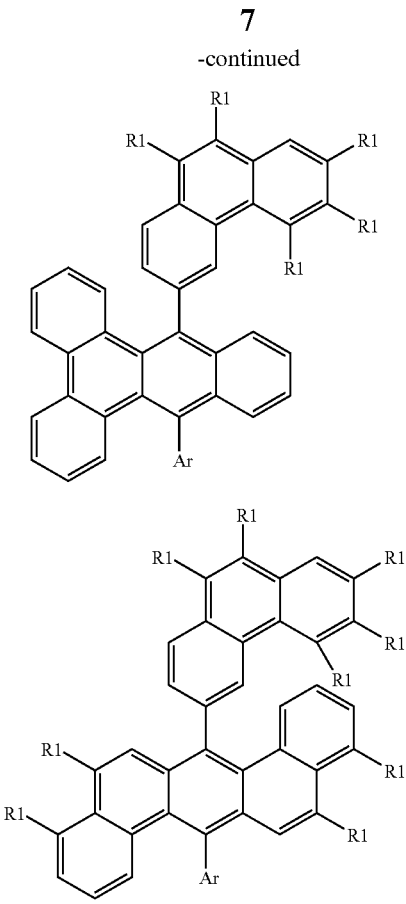

formula (7)

where Ar and R1 have the same meaning as described above.

The Ar group in formula (5) preferably stands for H or D.

In the formulae (2)-(4), (6) and (7), the Ar group preferably stands for an aromatic or heteroaromatic ring system having 5 to 30 aromatic ring atoms, which may be substituted by one or more non-aromatic radicals R1. The Ar group is particularly preferably built up from the aromatic or heteroaromatic groups benzene, naphthalene, anthracene, carbazole, phenanthrene, benzanthracene, chrysene, pyrene, phenanthroline, triazine and benzimidazole. Very particularly preferred Ar groups are selected from phenyl, ortho-, meta- or para-biphenyl, 1- or 2-naphthyl, 2-, 3- or 9-phenanthrenyl, para-phenylene-1-naphthyl, para-phenylene-2-naphthyl, 2-fluorenyl or 2-spirobifluorenyl, which may each be substituted by one or more non-aromatic radicals R1, or the Ar group is selected from the following formulae (8), (9), (10) and (11):

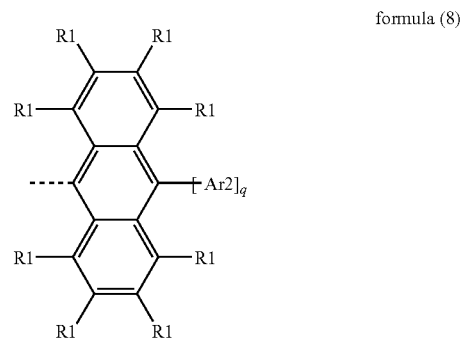

formula (8)

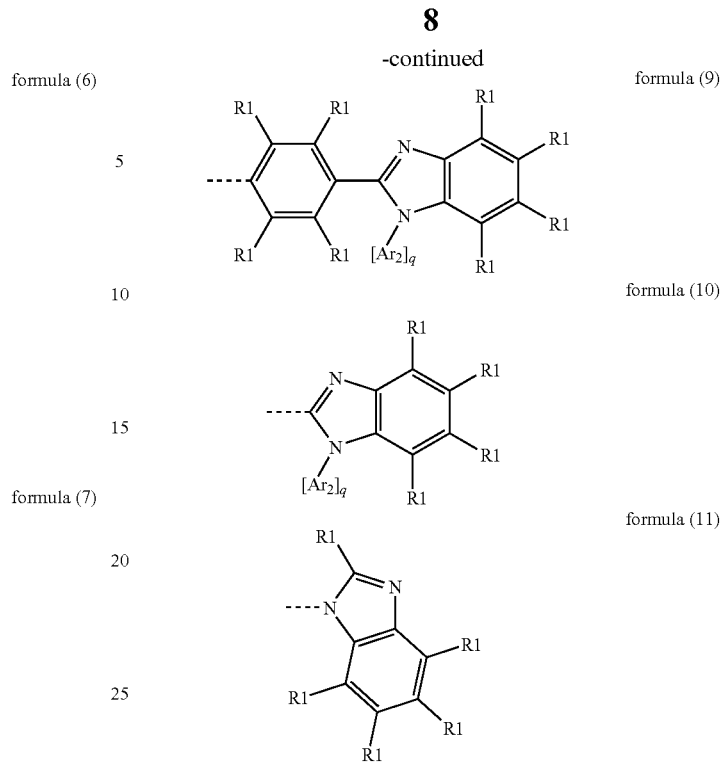

where R1 has the meaning given above, and furthermore:

Ar2 is an aryl or heteroaryl group having 5 to 16 aromatic ring atoms, preferably phenyl, 1-naphthyl, 2-naphthyl, 9-anthryl, chrysenyl, 1-pyrenyl, 2-pyrenyl, 2-phenanthrenyl, 3-phenanthrenyl, 9-phenanthrenyl, 2-benzimidazole or fluoranthenyl, which may each be substituted by one or more radicals R1;

q is 0, 1, 2 or 3, preferably 1 or 2, particularly preferably 1.

The symbols R1 and R2 in compounds of the formula (1) and in compounds of the formulae (2) to (7) preferably stand, identically or differently on each occurrence, for H, F, $N(Ar1)_2$, $C(=O)Ar1$, $P(Ar1)_2$, $P(=O)(Ar1)_2$, $S(=O)Ar1$, $S(=O)_2Ar1$, $CR3=CR3Ar1$, $Si(R3)_3$, $B(OAr1)_2$, $B(OR3)_2$, a straight-chain alkyl or alkoxy group having 1 to 20 C atoms or a branched or cyclic alkyl or alkoxy group having 3 to 20 C atoms, which may each be substituted by one or more radicals R3, where one or more non-adjacent $CH_2$ groups may be replaced by $R3C=CR3$, $C\equiv C$, $Si(R3)_2$, $C=O$, $P(=O)(R3)$, SO, $SO_2$, NR3, O or S and where one or more H atoms may be replaced by F, or an aromatic or heteroaromatic ring system having 5 to 40 aromatic ring atoms, which may each be substituted by one or more non-aromatic radicals R1, or a combination of these systems. The radicals R2 in compounds of the formula (1) furthermore preferably form an aromatic ring system. The symbols R1 and R2 in the compounds of the formula (1) and in compounds of the formulae (2) to (7) particularly preferably stand, identically or differently on each occurrence, for H, F, $N(Ar1)_2$, $C(=O)Ar1$, $P(=O)(Ar1)_2$, $S(=O)Ar1$, $CR3=CR3Ar1$, $Si(R3)_3$, $B(OAr1)_2$, $B(OR3)_2$, a straight-chain alkyl group having 1 to 10 C atoms or a branched or cyclic alkyl group having 3 to 10 C atoms, which may each be substituted by one or more radicals R3, where one or more non-adjacent $CH_2$ groups may be replaced by $R3C=CR3$, $C\equiv C$, NR3 or O and where one or more H atoms may be replaced by F, or an aromatic or heteroaromatic ring system having 5 to 30 aromatic ring atoms, which may each be substituted by one or more non-aromatic radicals R1, or a combination of these systems.

Examples of preferred compounds of the formula (1) or of the formulae (2) to (7) are structures (1) to (122) depicted below.
(1)
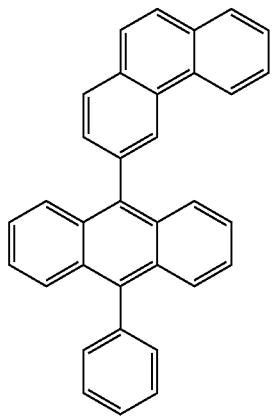
(2)
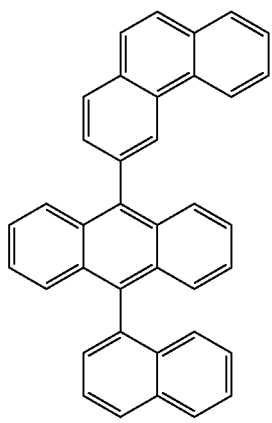
(3)
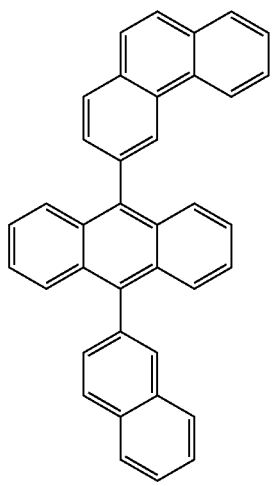
(4)
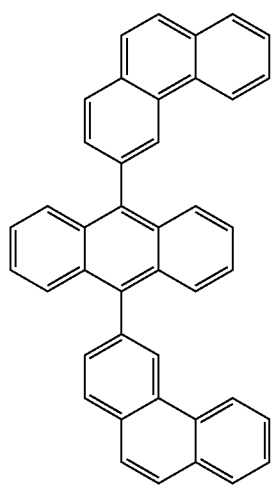
(5)
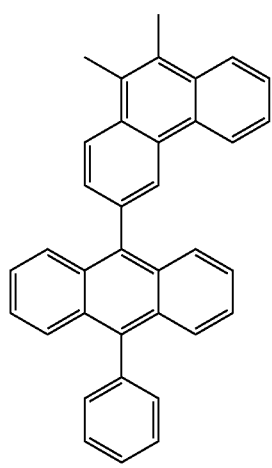
(6)
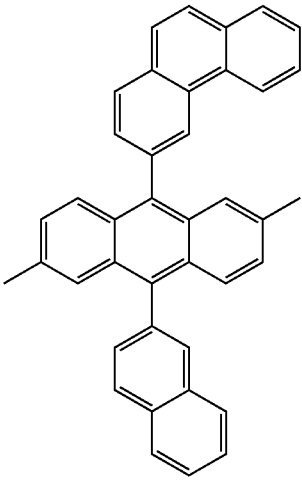

(7)
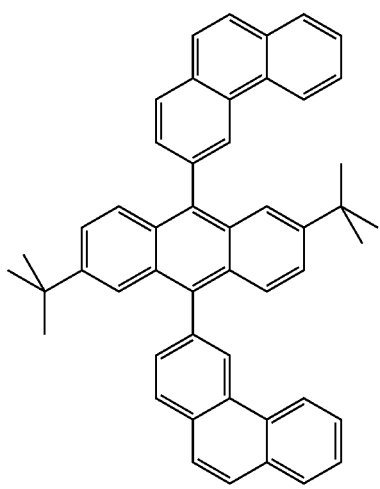
(8)
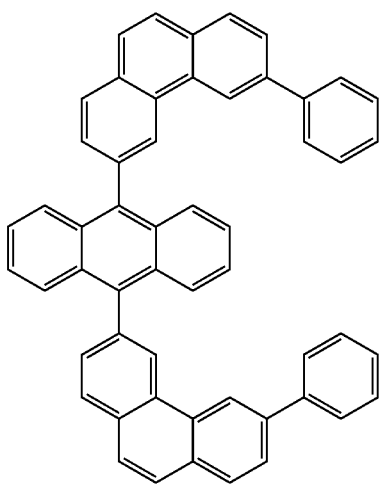
(9)
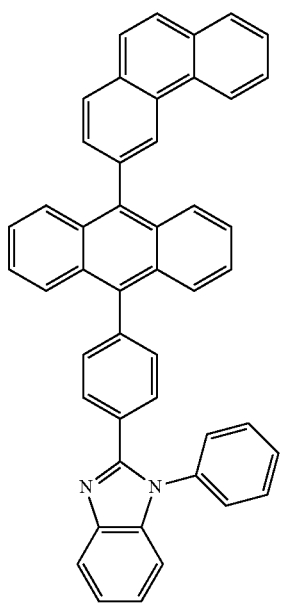
(10)
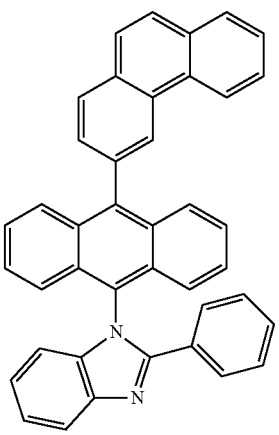
(11)
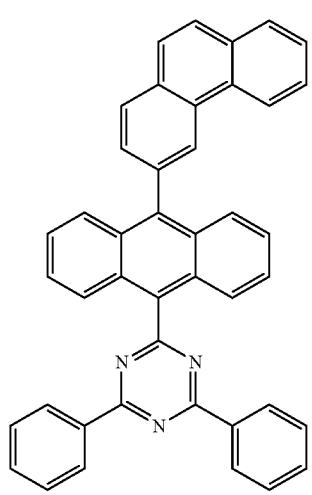
(12)
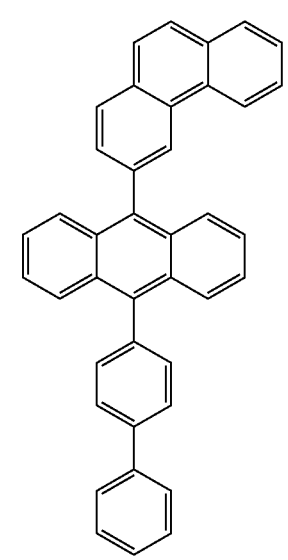

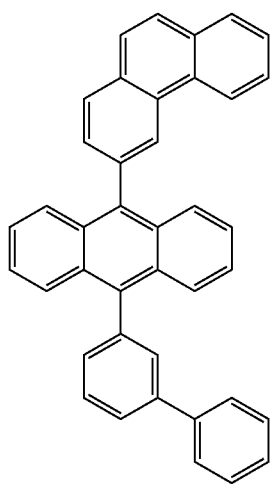
(13)
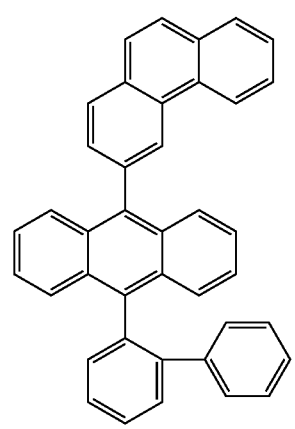
(14)
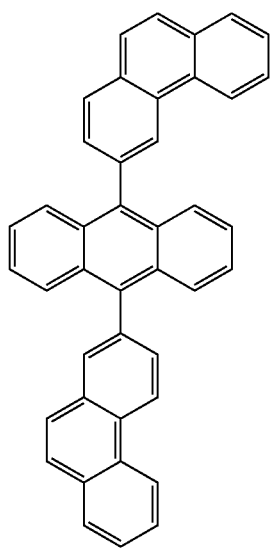
(15)
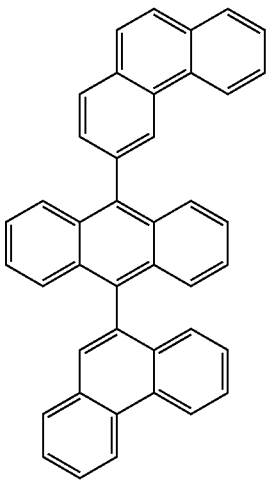
(16)
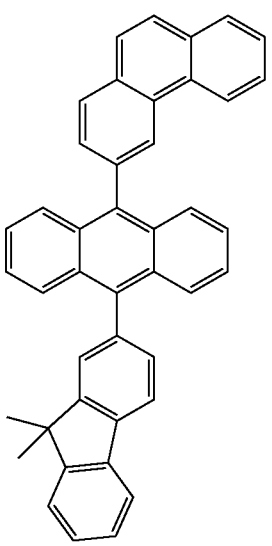
(17)
(18)

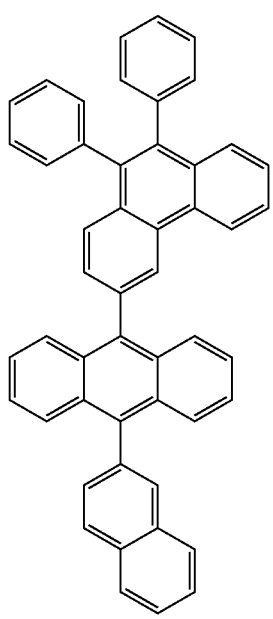
(19)
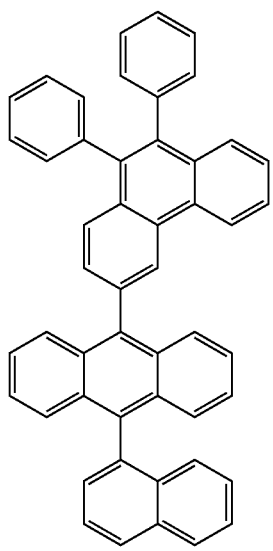
(20)
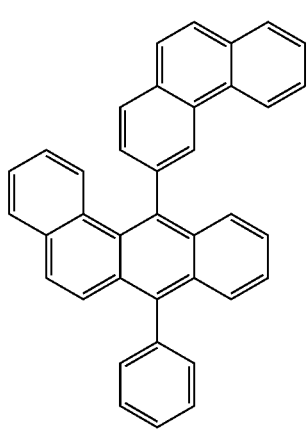
(21)
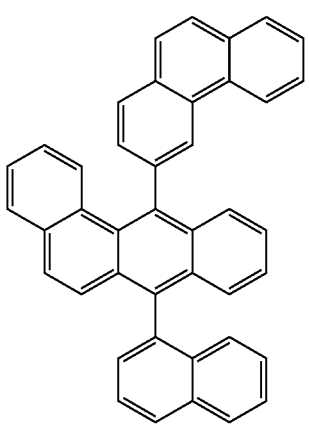
(22)
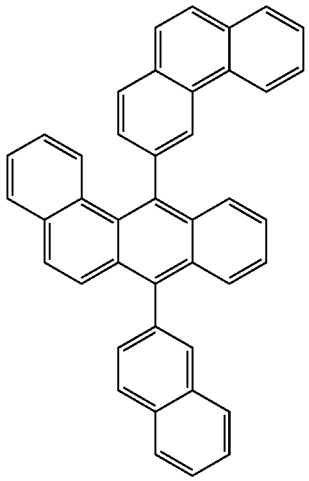
(23)
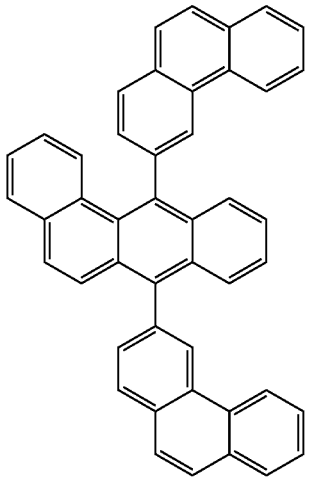
(24)

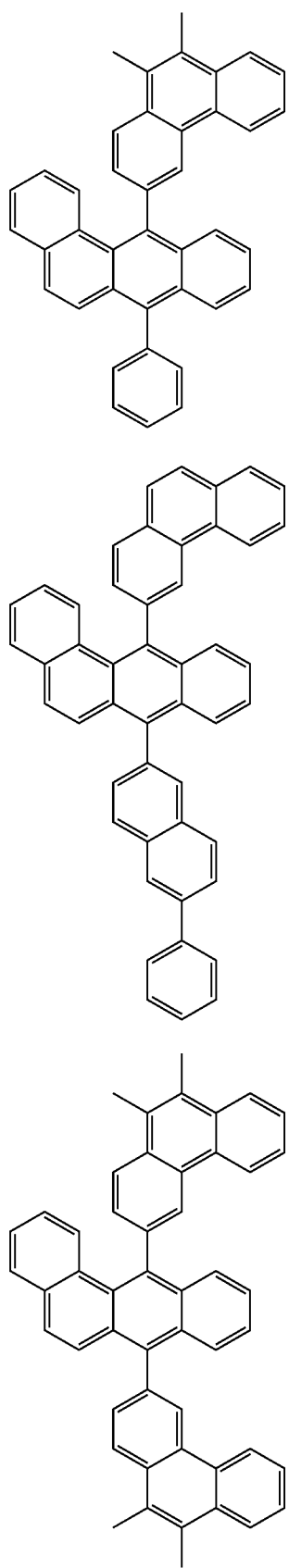
(25)
(26)
(27)
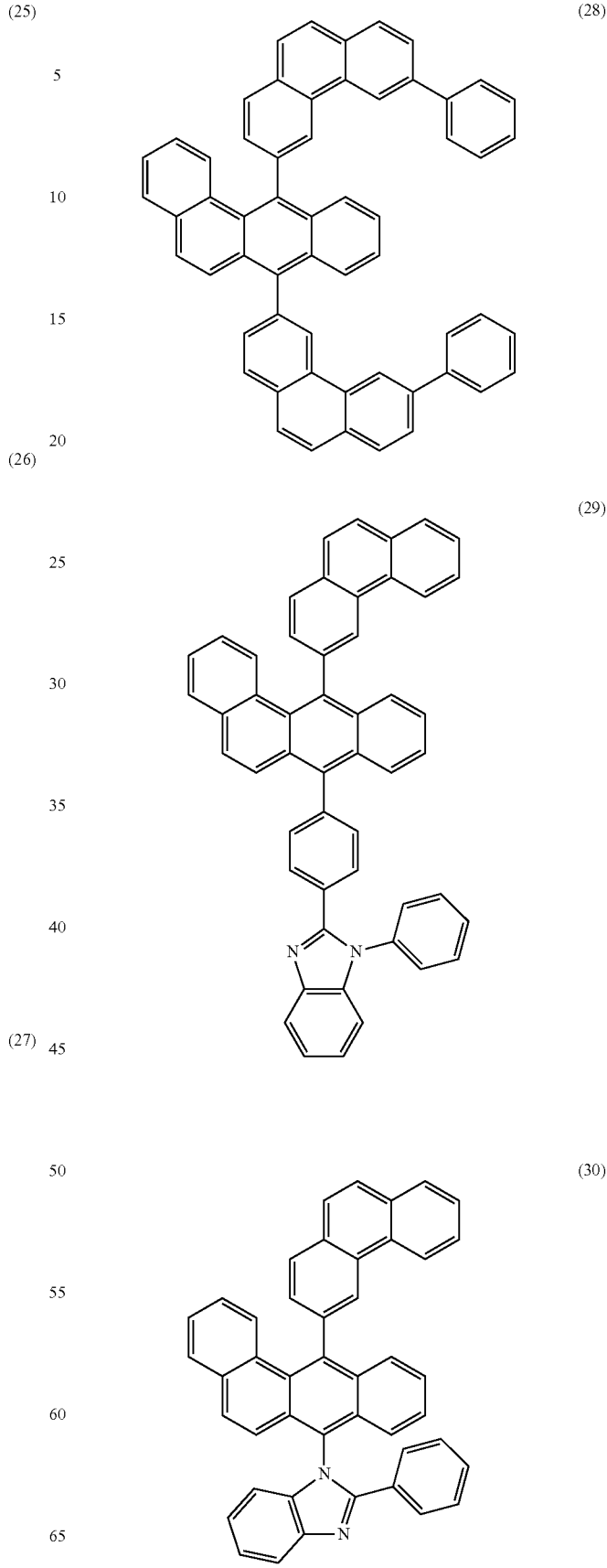
(28)
(29)
(30)

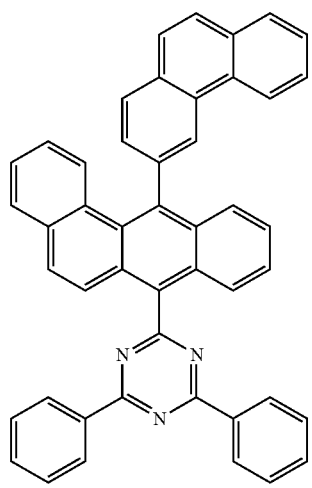
(31)
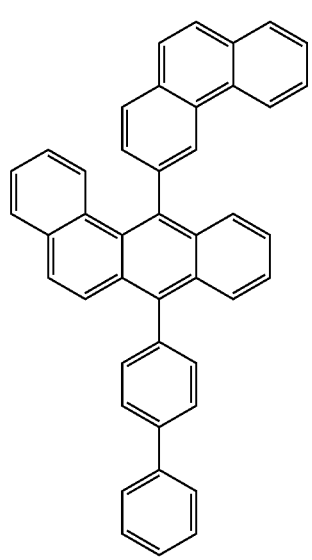
(32)
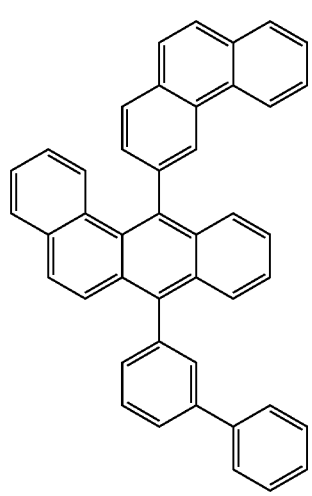
(33)
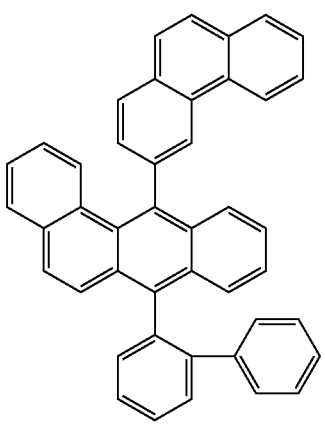
(34)
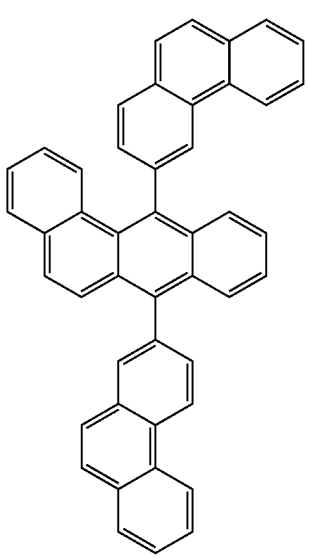
(35)
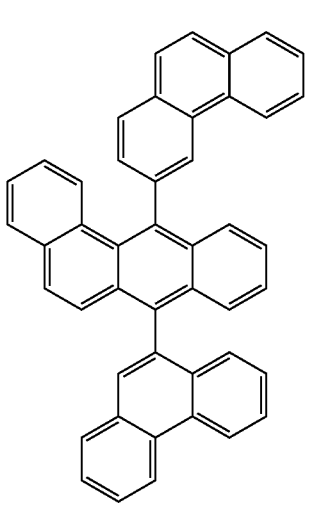
(36)

(37)
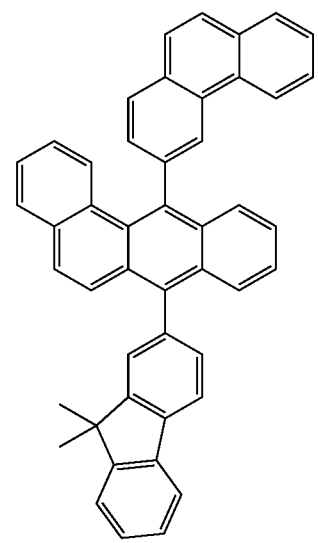
(38)
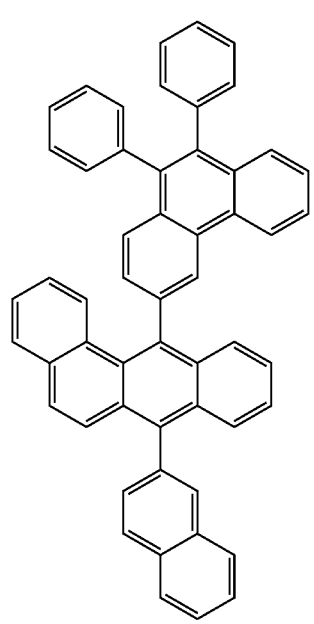
(39)
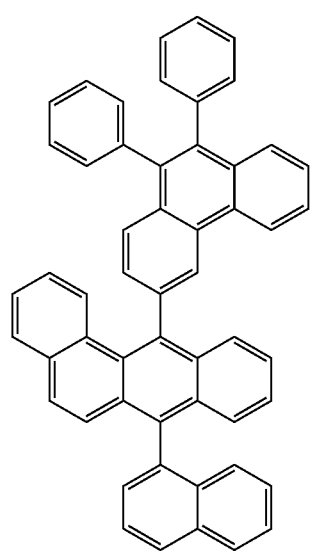
(40)
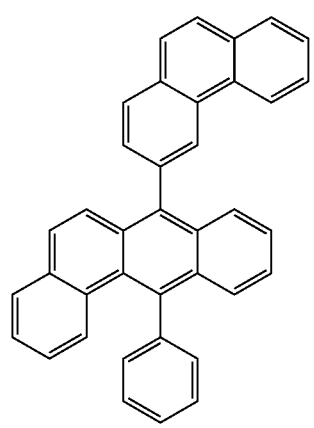
(41)

(42)
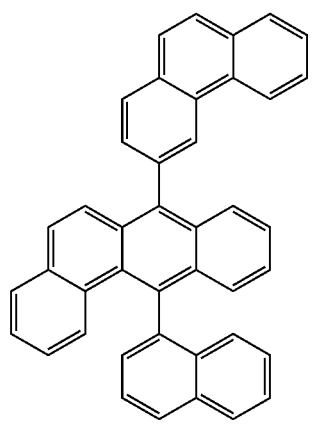
(43)
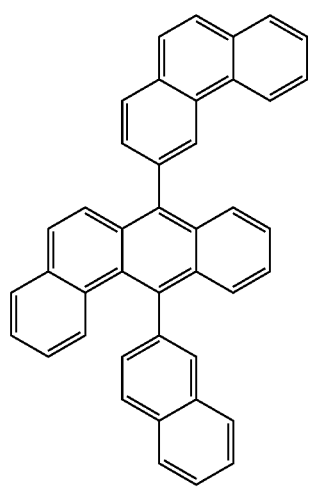
(44)
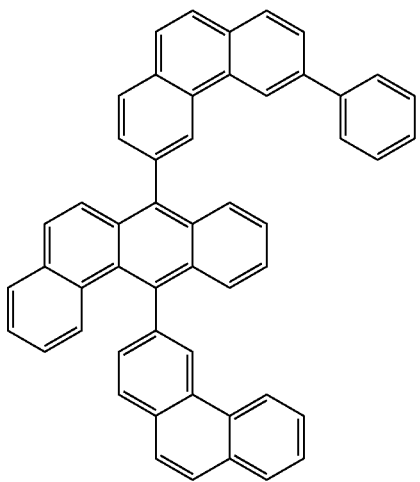
(45)
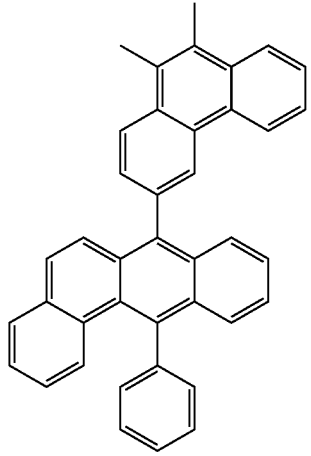
(46)
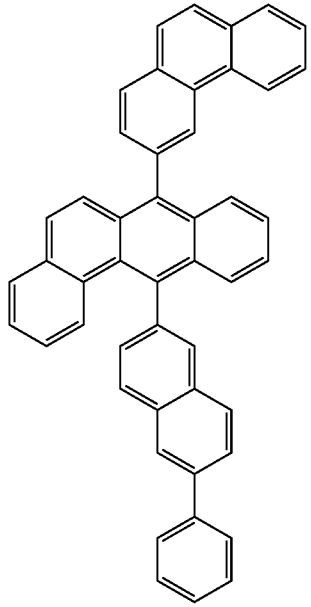
(47)
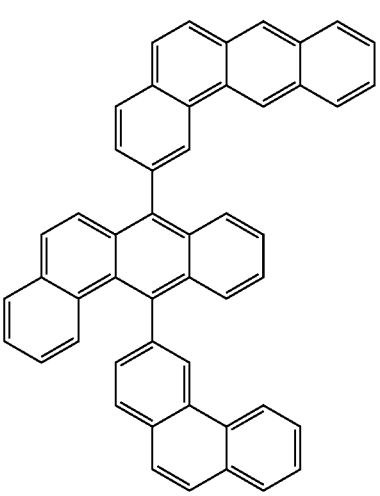

(48)
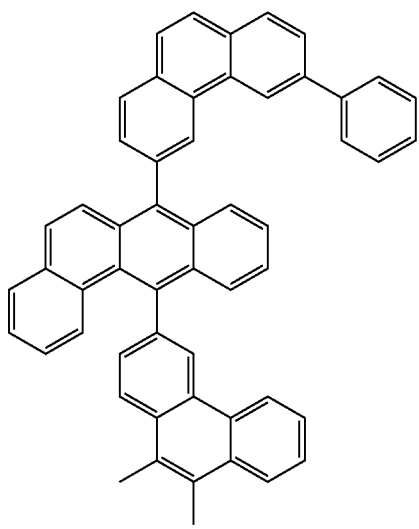
(49)
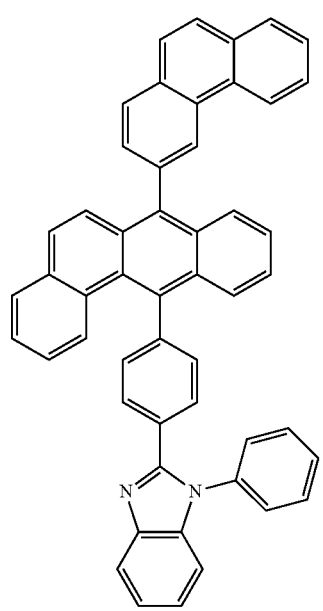
(50)
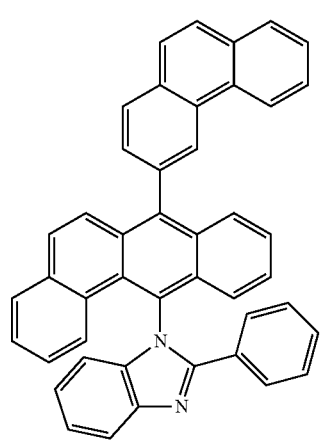
(51)
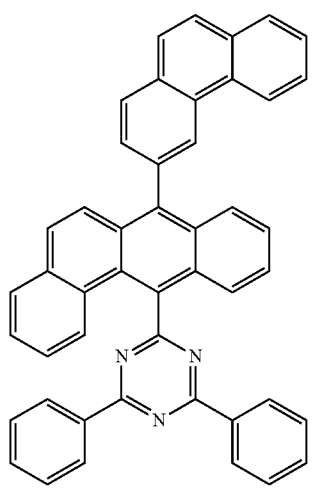
(52)
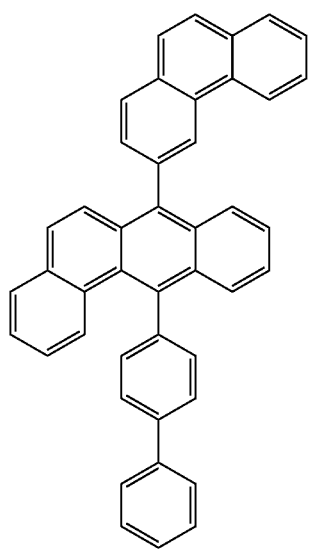
(53)
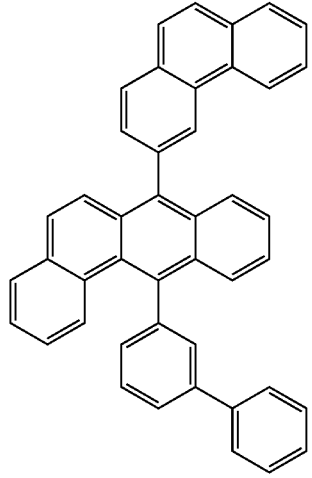

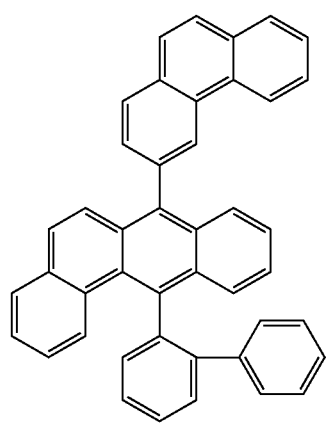
(54)
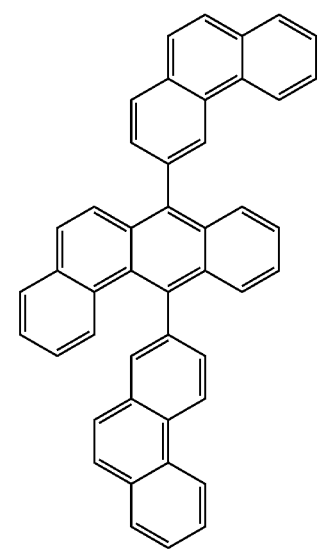
(55)
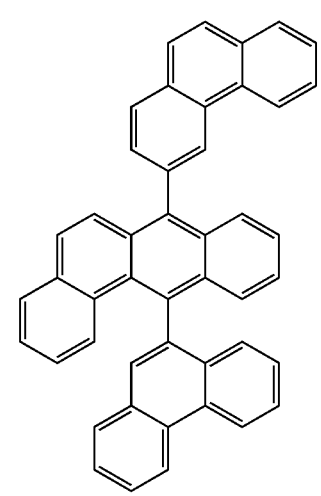
(56)
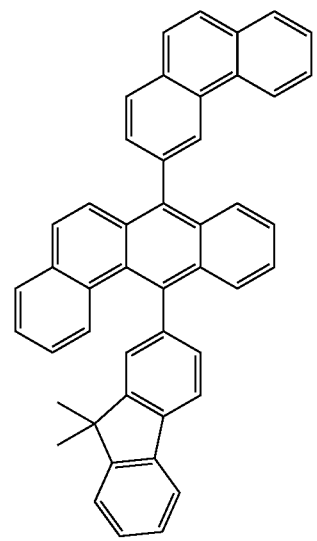
(57)
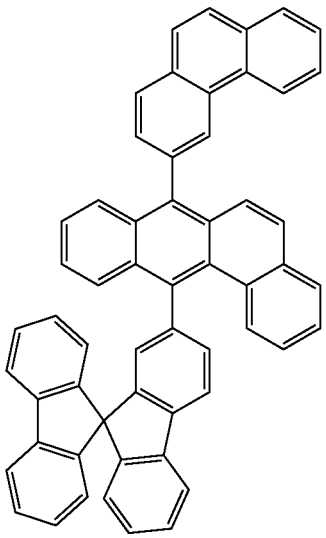
(58)

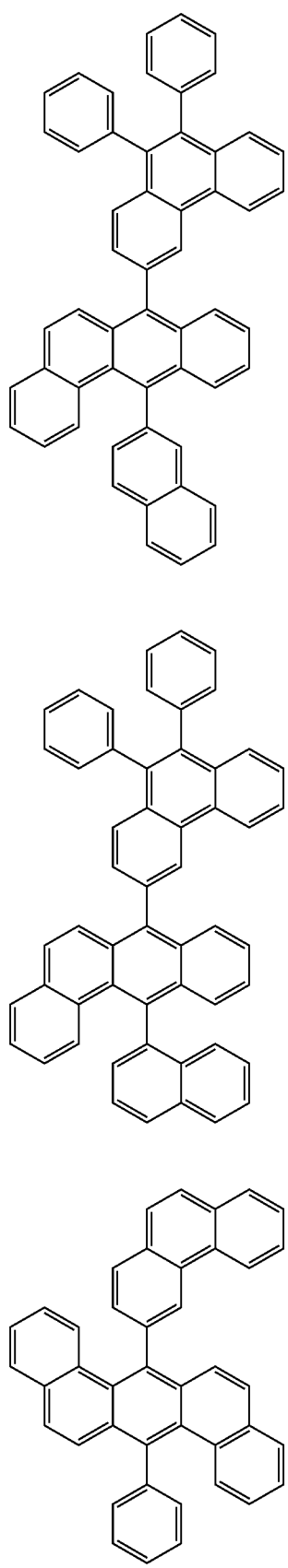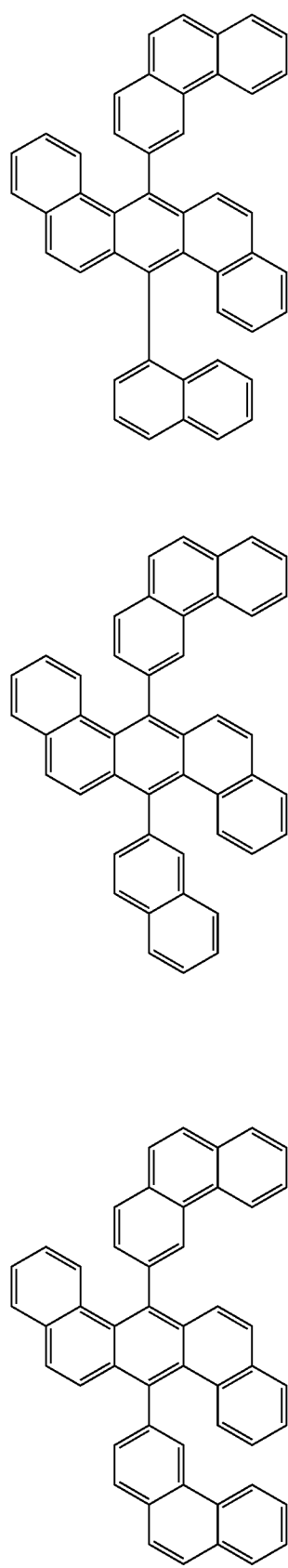

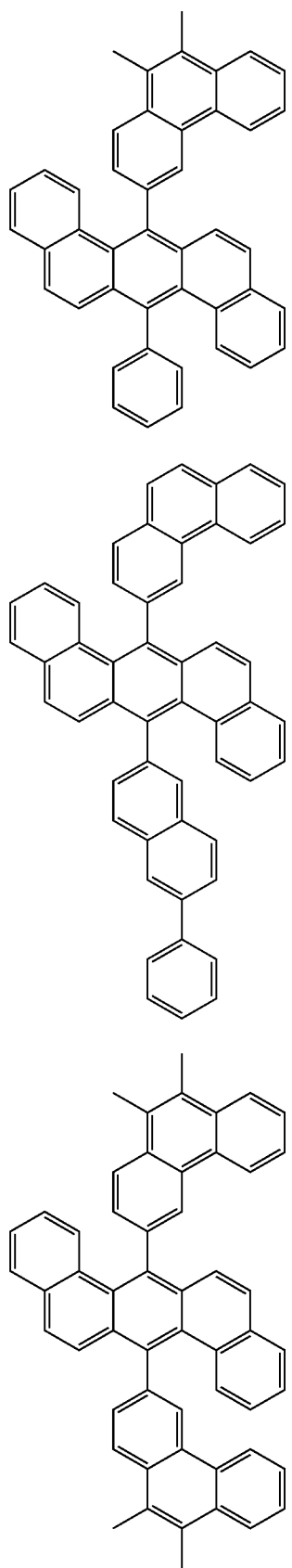
(65)
(66)
(67)
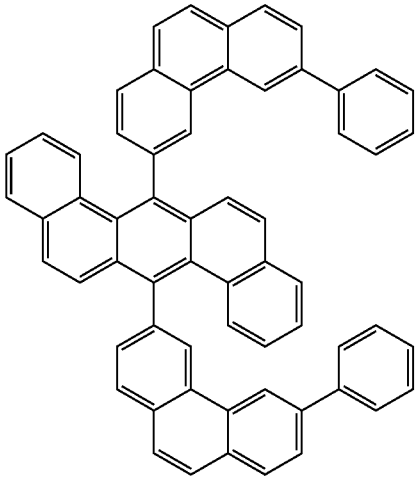
(68)
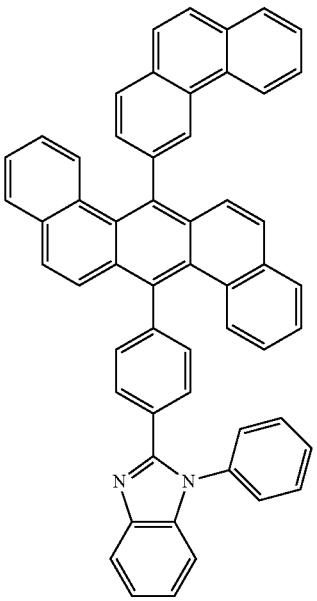
(69)
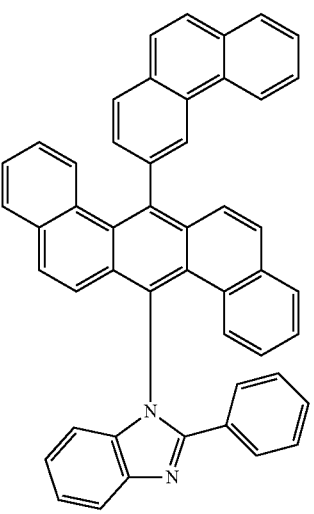
(70)

(71)
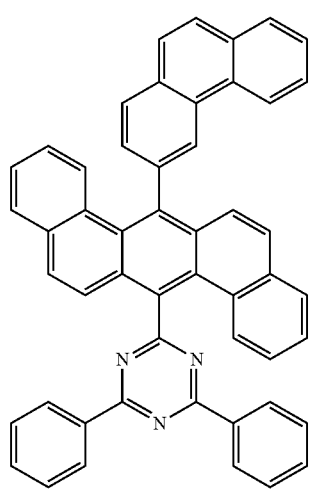
(72)
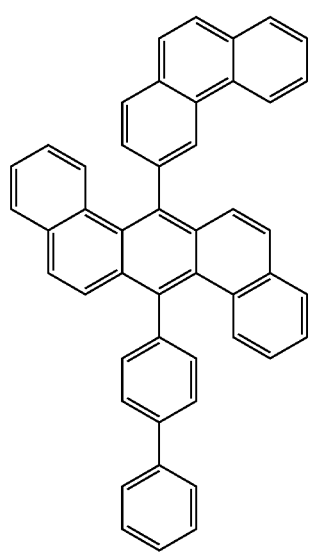
(73)
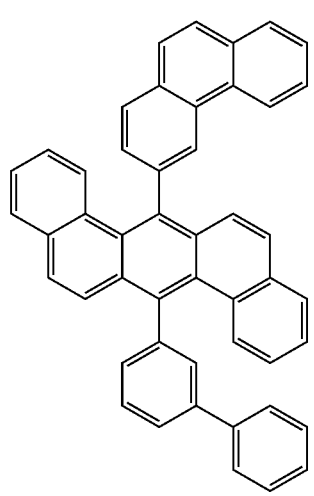
(74)
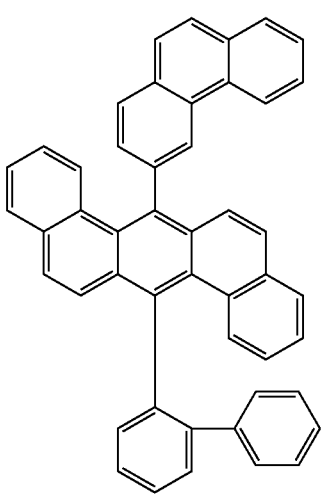
(75)
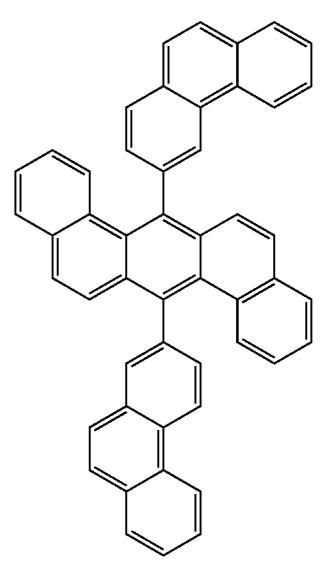
(76)
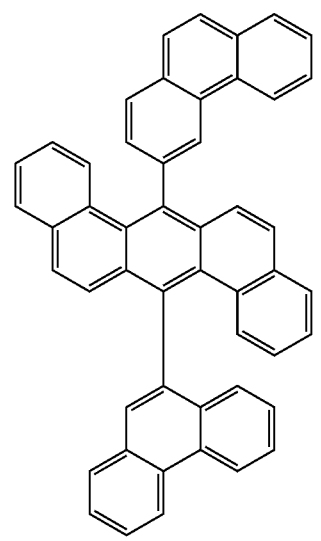

(77)
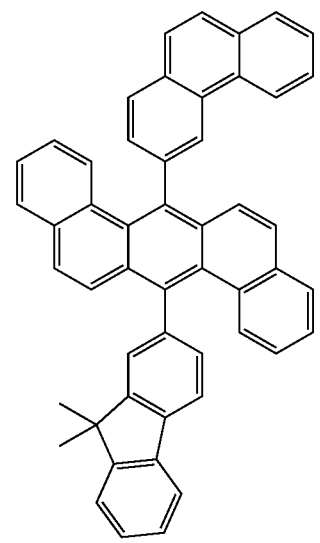
(78)
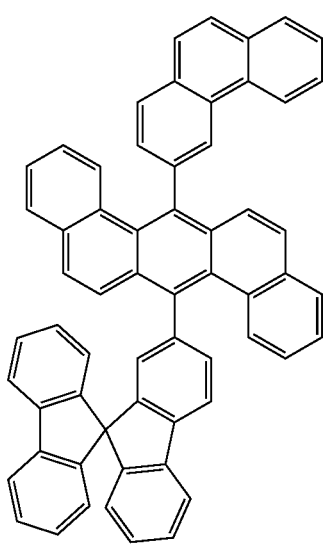
(79)
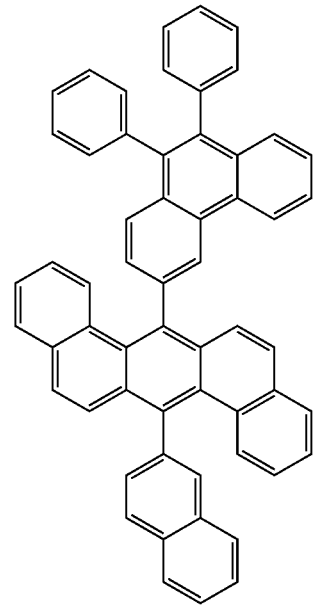
(80)
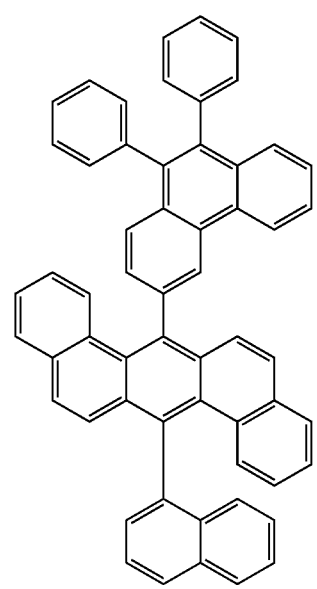
(81)
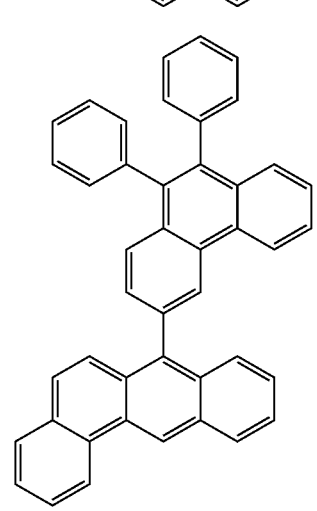

(82)
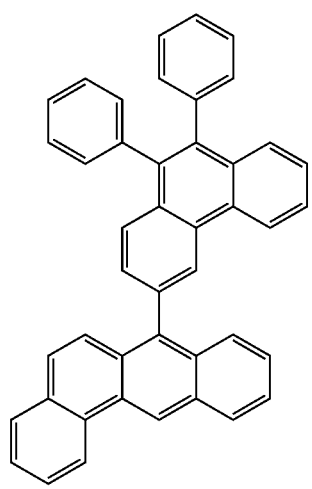
(83)
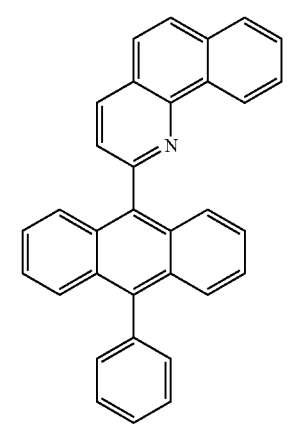
(84)
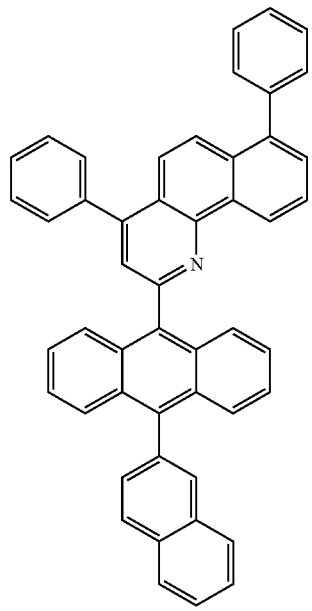
(85)
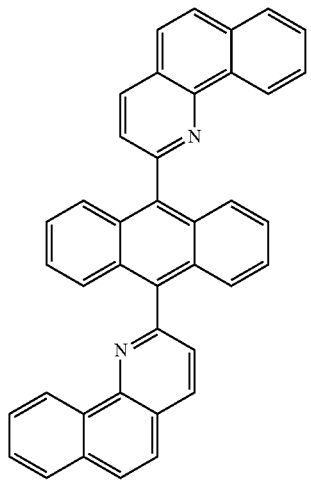
(86)
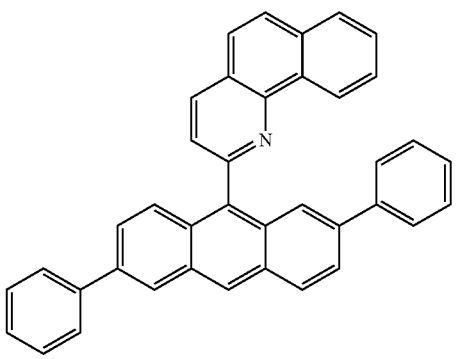
(87)
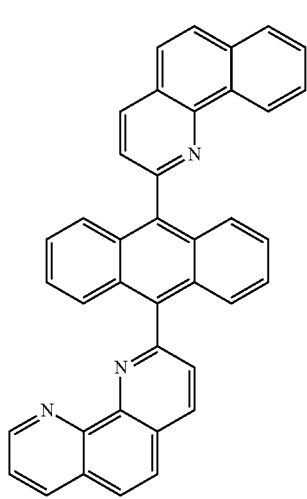

-continued
(88)
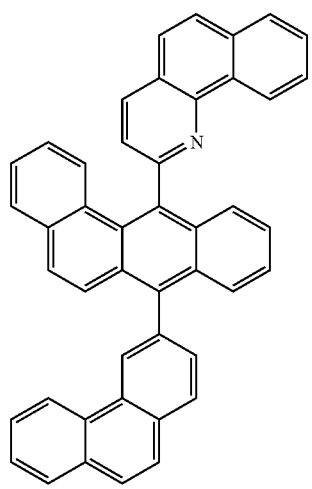
(89)
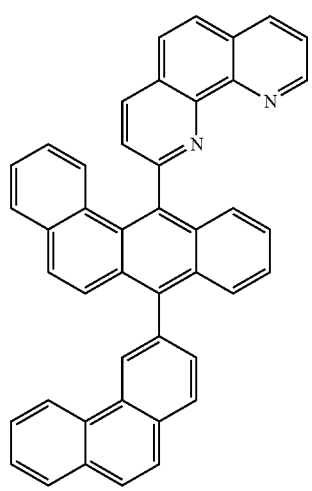
(90)
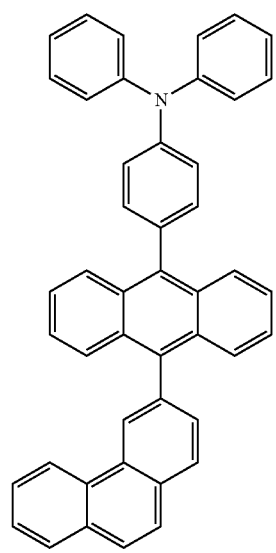
-continued
(91)
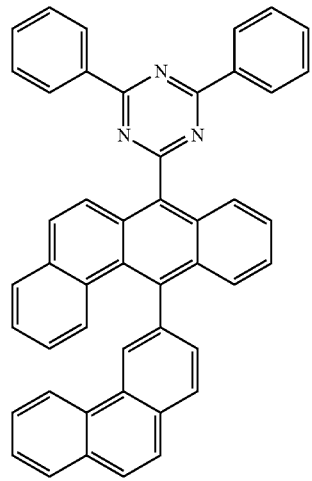
(92)
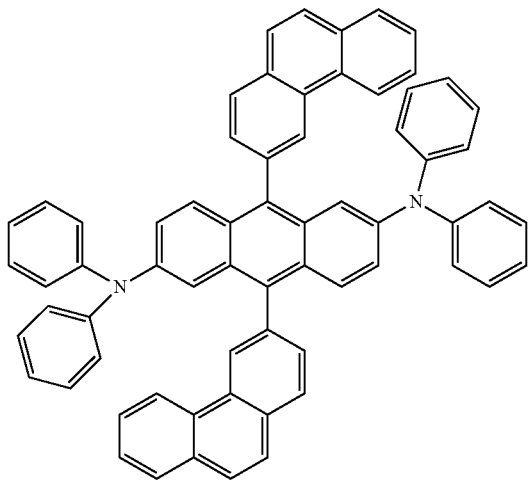
(93)
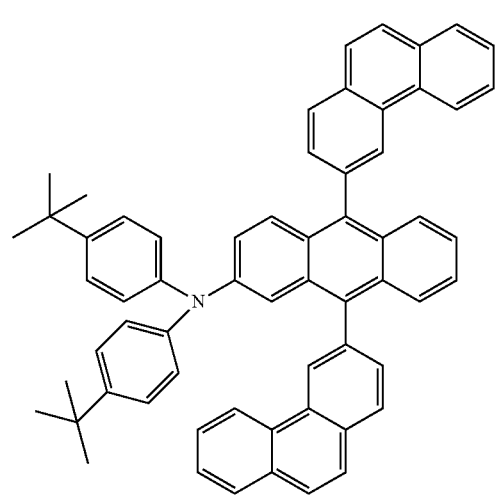

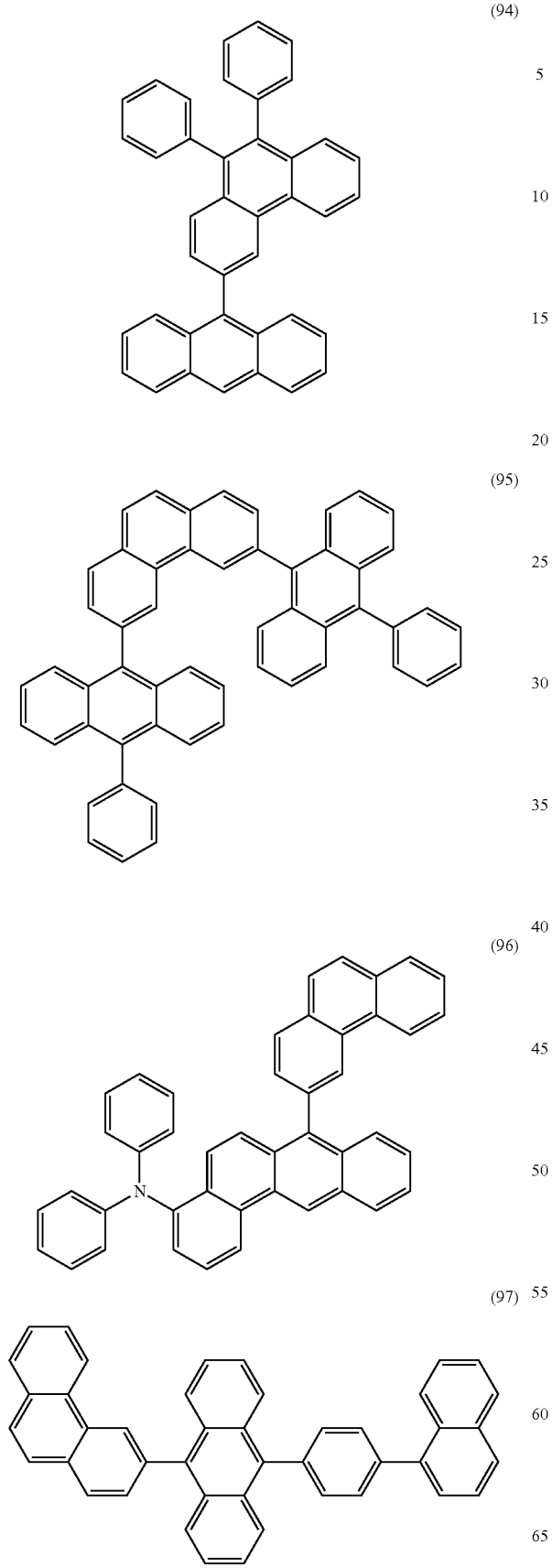
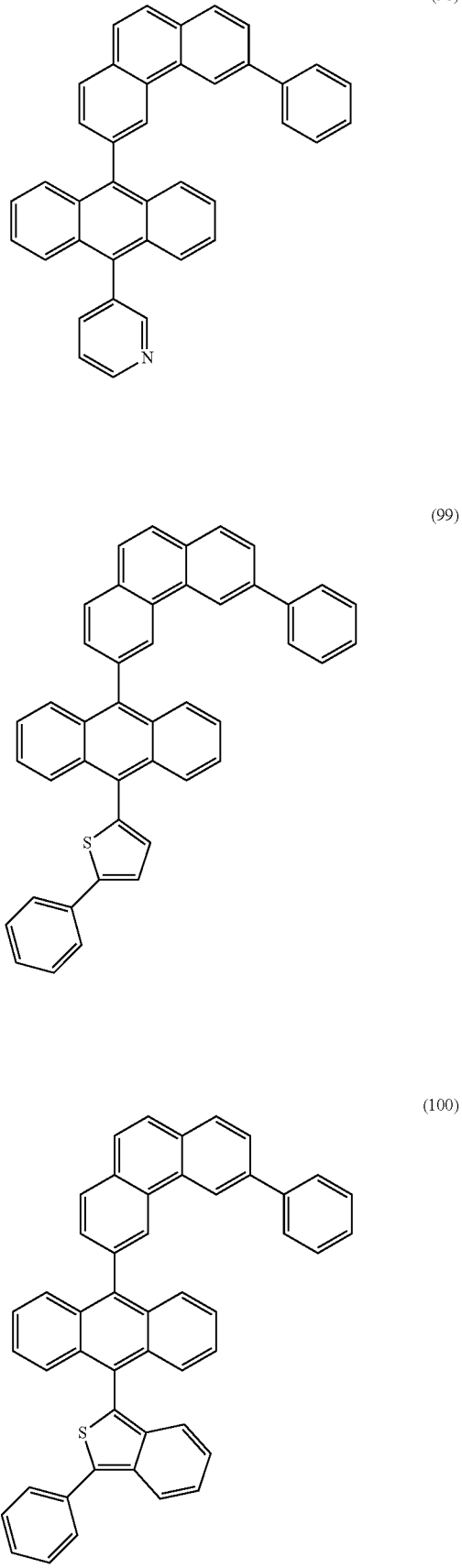

(101)
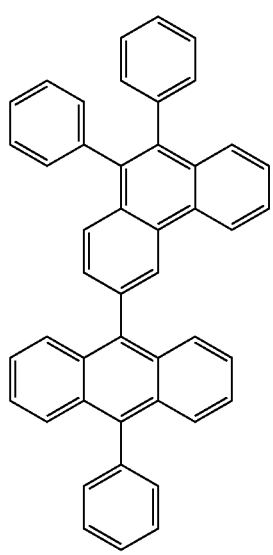
(102)
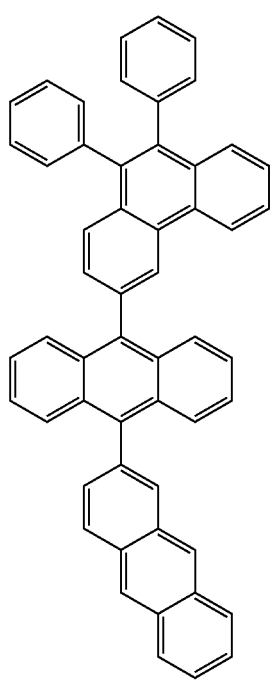
(103)
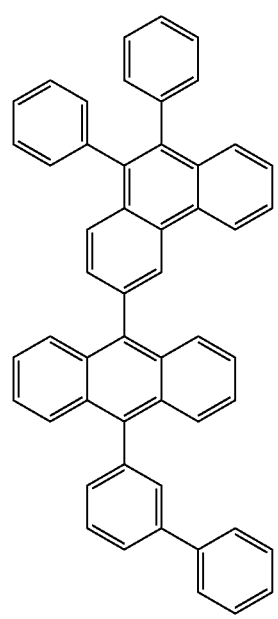
(104)
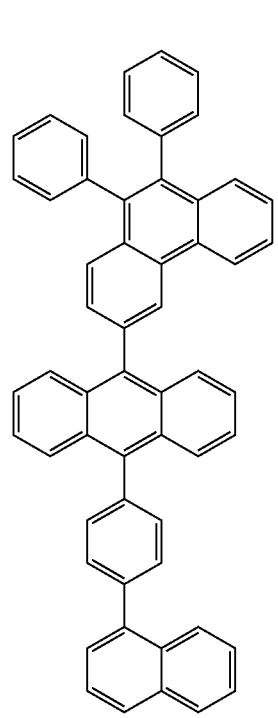

(105)
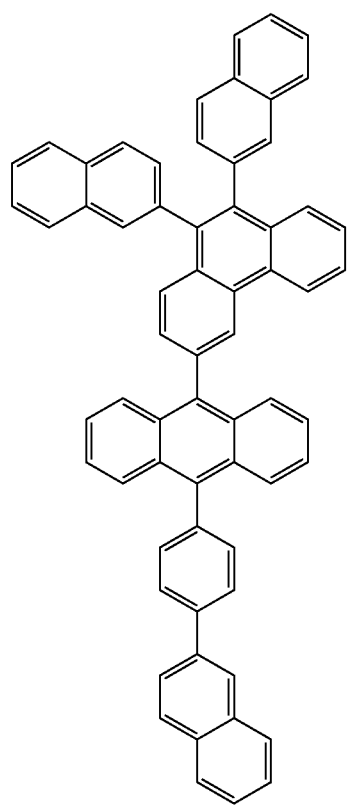
(107)]
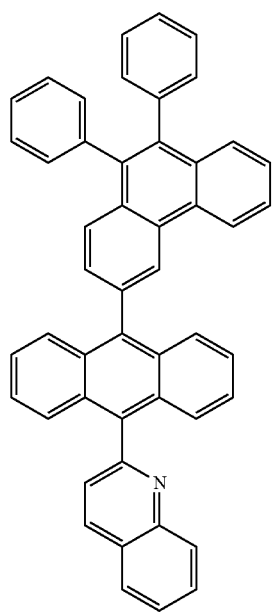
(106)
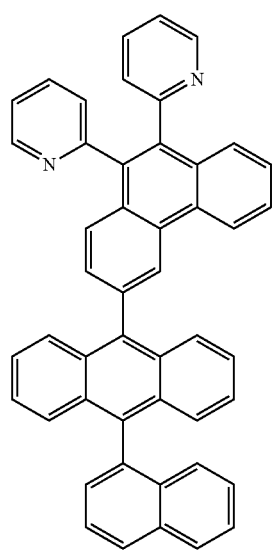
(108)
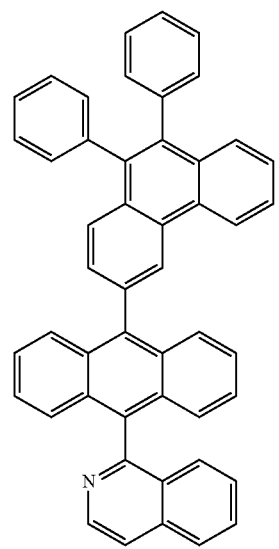

(109)
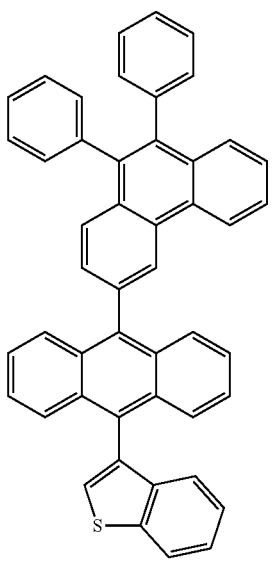
(110)
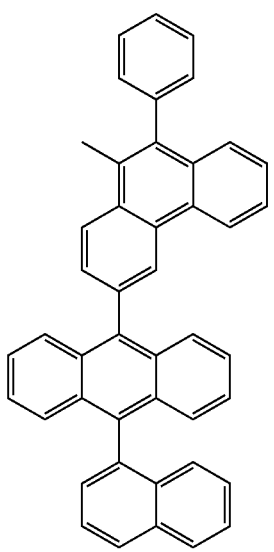
(111)
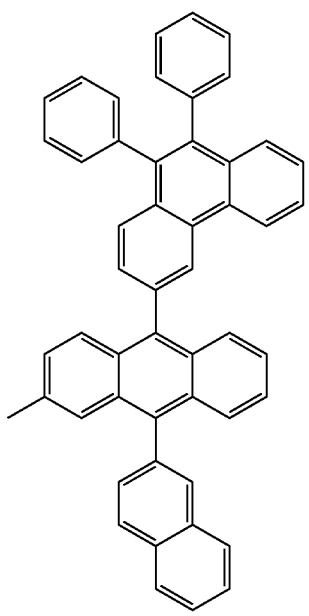
(112)
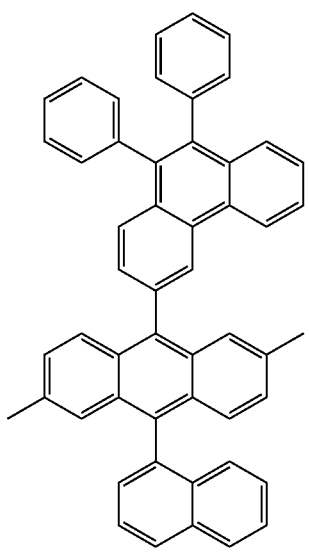

(113)
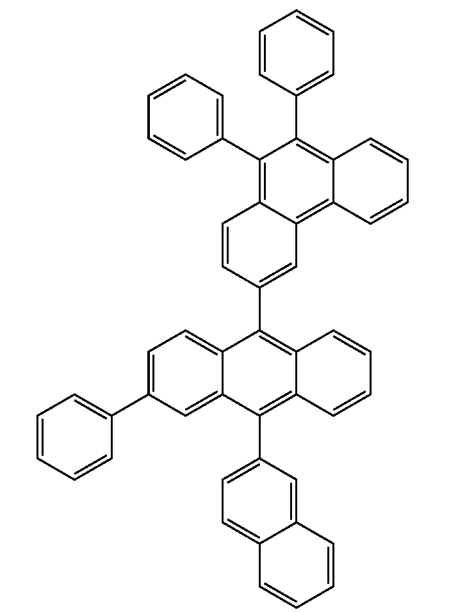
(114)
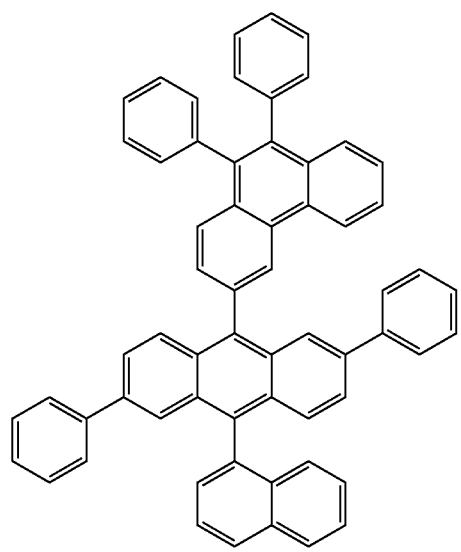
(115)
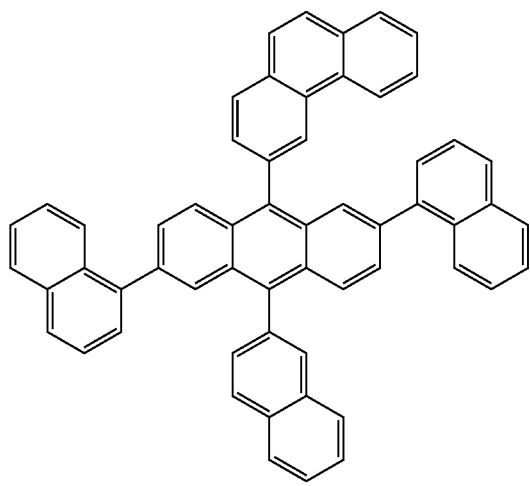
(116)
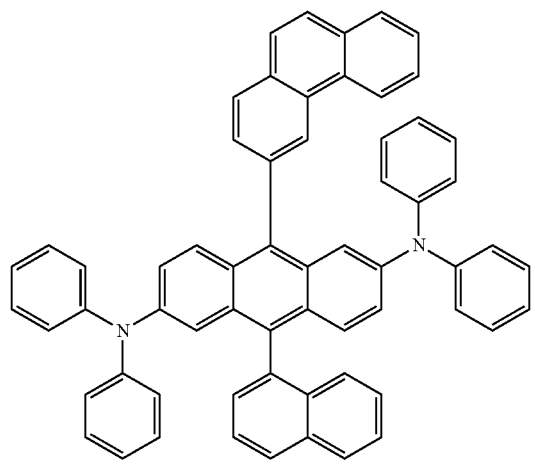
(117)
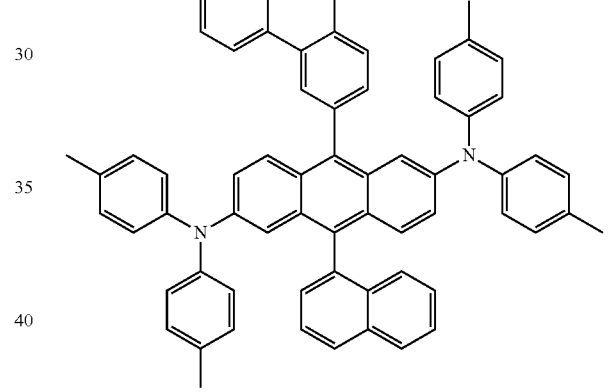
(118)
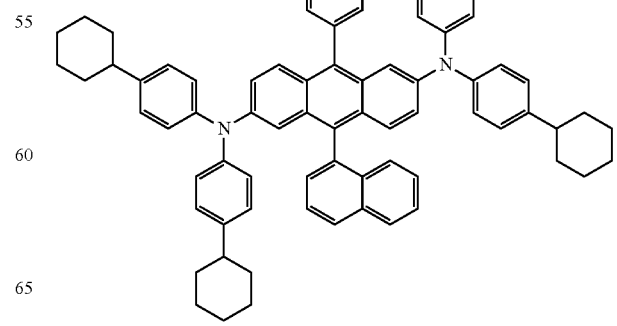

(119)
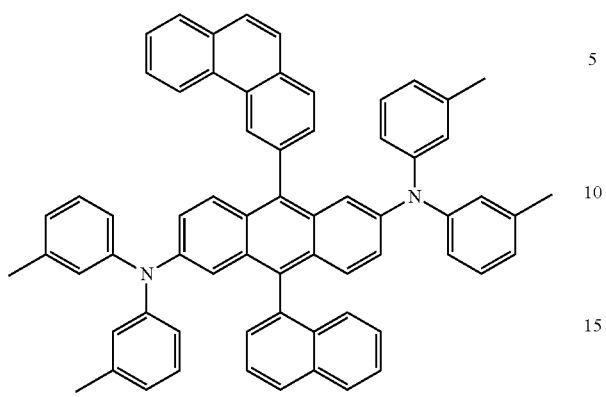

(120)
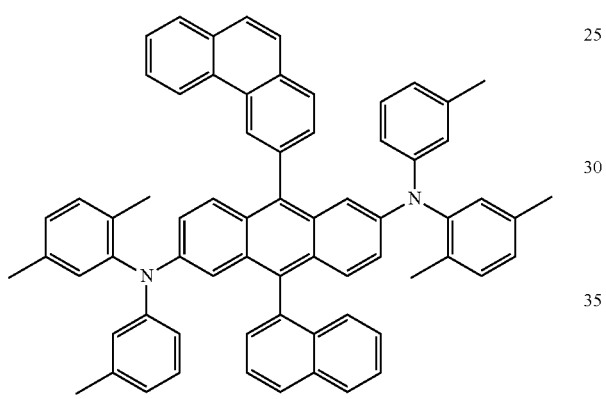

(121)
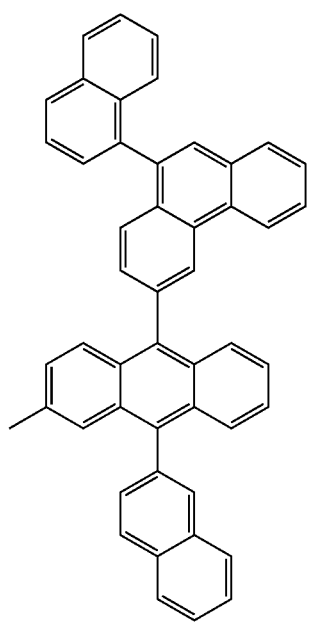

(122)
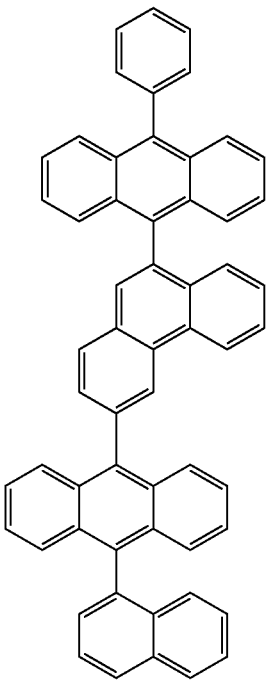

The compounds of the formula (1) according to the invention can be prepared by synthetic steps which are generally known to the person skilled in the art. The starting compound used can be, for example, the corresponding 3-bromophenanthrenes and 9-bromoanthracenes or 9,10-dibromoanthracenes or 7- or 12-bromobenz[a]anthracene or 7,12-dibromobenz[a]-anthracene. The compounds substituted by corresponding leaving groups, such as chlorine, iodine, triflate or tosylate, can likewise serve as starting compounds, which are then optionally converted into the corresponding boronic acid derivatives. The Suzuki coupling of the compounds can be carried out under standard conditions, as are known to the person skilled in the art of organic chemistry.

3-Bromine-substituted phenanthrenes can be prepared, as shown in Scheme 1, by a modified Pschorr phenanthrene synthesis. This consists, in a first step, of a stereospecific Perkin condensation of ortho-nitrobenzaldehyde and para-bromophenylacetic acid (Scheme 1a). The nitro group of the nitrocinnamic acid derivative obtained in the first step is reduced to the amino group, for example by iron (II) (Scheme 1b). In a final step, the cinnamic acid derivative is converted, after diazotisation, into the corresponding 3-bromophenanthrene in an intramolecular Sandmeyer reaction in the presence of copper powder (Scheme 1c) (D. W. Scott, R. A. Bunce, N. F. Materer, *Organic Preparations and Procedures* 2006, 38 (3), 325-346; W. Fleischhacker, F. Vieböck, *Monatshefte der Chemie* 1965, 96 (5), 1512-1519).

53

Scheme 1

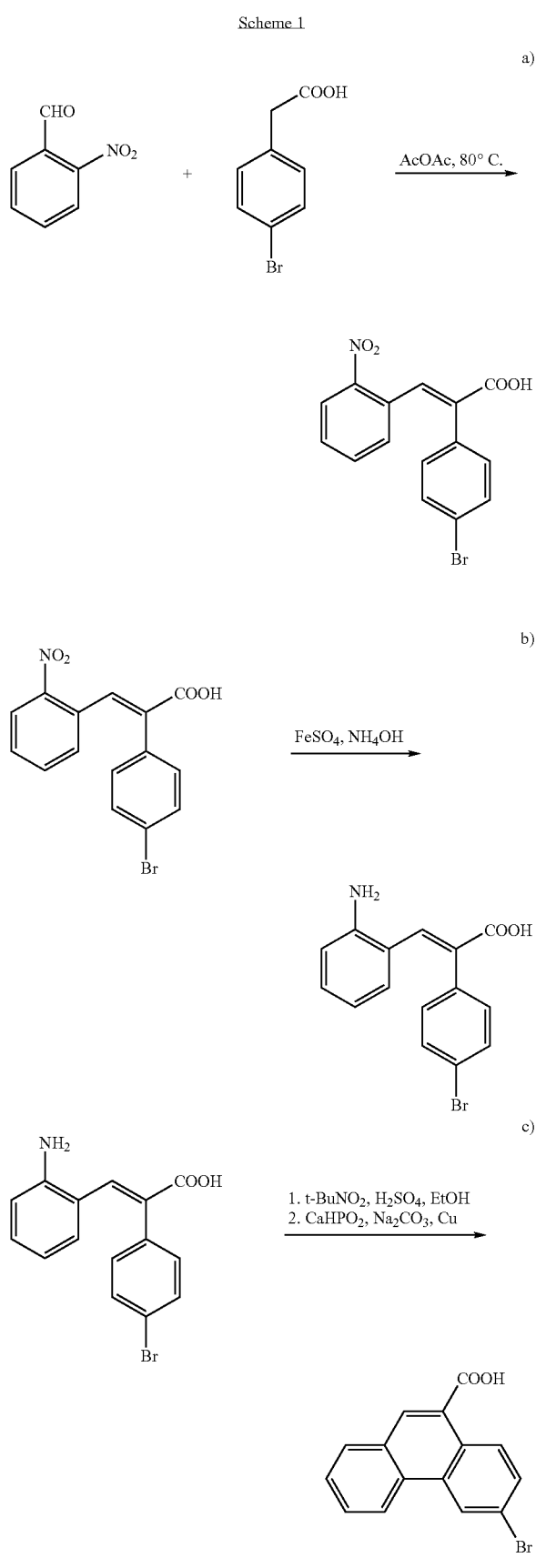

54

This phenanthrene derivative, which is also substituted by a carboxyl group, is now available for further coupling reactions. It is of course also possible to synthesise corresponding substituted 3-bromophenanthrene derivatives by the use of substituted starting compounds.

The synthesis of the anthracene component is shown in Scheme 2 with reference to the example of 2-naphthylanthracene. It is of course also possible to select another aryl group instead of the 2-naphthyl group and/or the aryl group may be substituted. It is likewise possible to employ a substituted anthracene or a substituted or unsubstituted benzanthracene or tetracene instead of the unsubstituted anthracene. Starting from 9-bromoanthracene, the aromatic Ar group, here a 2-naphthyl group, is introduced as boronic acid derivative in a Suzuki coupling. This can be carried out under standard conditions, as are known to the person skilled in the art of organic synthesis. Other coupling reactions are of course likewise possible. The 9-arylanthracene derivative obtained in this way is functionalised in the 10-position, for example brominated, where the bromination can be carried out under standard conditions, as are known to the person skilled in the art of organic synthesis, for example using elemental bromine in acetic acid or chloroform or NBS in THF. The bromoanthracene can be converted into the boronic acid, for example by lithiation and reaction with $B(O^iPr)_3$.

Scheme 2:

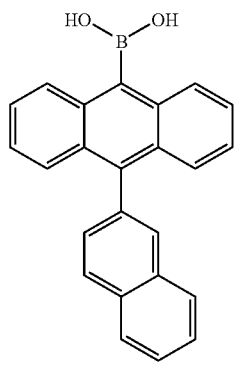

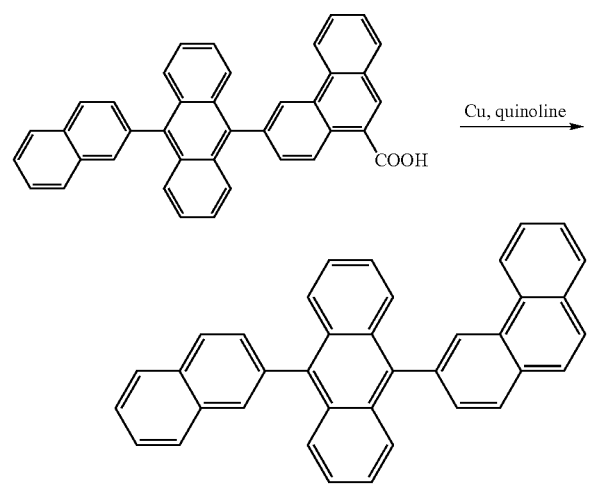

This boronic acid is now available for coupling to the 3-bromophenanthrene, as shown in Scheme 3. The Suzuki coupling here can be carried out under standard conditions of organic chemistry, for example using Pd(PPh$_3$)$_4$ as catalyst and sodium carbonate as base (Scheme 3a). In a final step, the carboxylic acid, which is still bonded to the phenanthrene, can now be cleaved off, for example by the action of copper and quinoline (Scheme 3b).

Scheme 3:

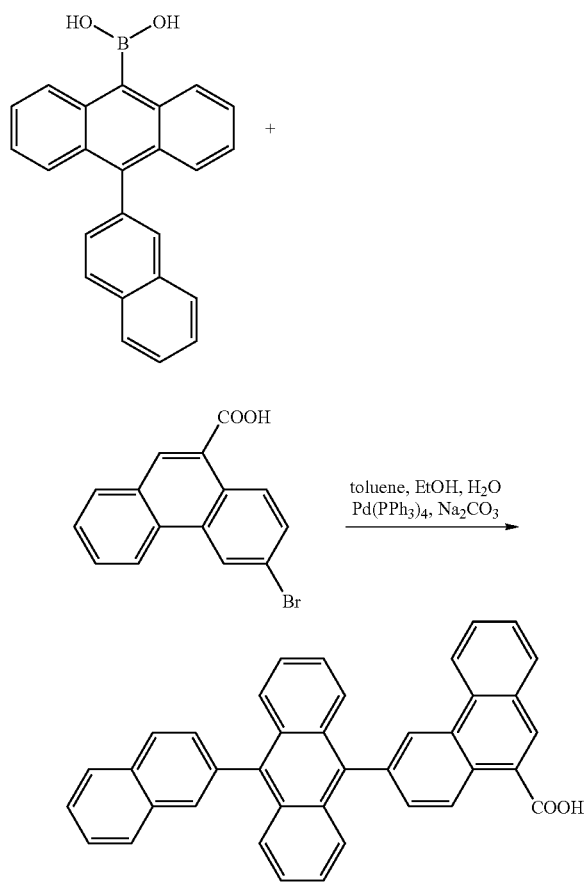

The present invention furthermore relates to a process for the preparation of compounds of the formula (1) by coupling a 9-aryl-substituted anthracene which is substituted in the 10-position by a reactive leaving group, in particular chlorine, bromine, iodine, triflate, tosylate, boronic acid or boronic acid ester, or a corresponding benz[a]anthracene or tetracene to a phenanthrene derivative which is functionalised in the 3-position, in particular by chlorine, bromine, iodine, triflate, tosylate, boronic acid or boronic acid ester. Both the phenanthrene and also the anthracene, benzanthracene or tetracene may also be substituted here by the substituents R1 or R2 shown above. Particularly preferably, one component contains bromine as functional leaving group and the other component contains a boronic acid or a boronic acid ester as functional leaving group. Suitable coupling reactions are, in particular, transition-metal-catalysed coupling reactions, in particular the Suzuki coupling with palladium catalysis.

The compounds of the formula (1) are suitable for use in electronic devices, in particular in organic electroluminescent devices (OLEDs, PLEDs). Depending on the substitution, the compounds are employed in different functions and layers.

The invention therefore furthermore relates to the use of compounds of the formula (1) in electronic devices, in particular in organic electroluminescent devices.

The invention again furthermore relates to organic electronic devices comprising at least one compound of the formula (1), in particular organic electroluminescent devices comprising anode, cathode and at least one emitting layer, characterised in that at least one organic layer, which may be an emitting layer or another layer, comprises at least one compound of the formula (1). The organic electronic device here may also have inorganic layers.

Apart from cathode, anode and the emitting layer, the organic electroluminescent device may also contain further layers. These are selected, for example, from in each case one or more hole-injection layers, hole-transport layers, electron-transport layers, electron-injection layers and/or charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*). However, it should be pointed out that each of these layers does not necessarily have to be present. In a further embodiment of the invention, the organic electroluminescent device contains a plurality of emitting layers, where at least one organic layer comprises at least one compound of the formula (1). These emission layers preferably have in total a plurality of emission maxima between 380 nm and 750 nm, resulting overall in white emission, i.e. various emitting compounds which are able to fluoresce or phosphoresce and emit blue and yellow, orange or red light are used in the emitting layers. The compound of the formula (1) is preferably used here in a blue-emitting layer. Particular preference is given to three-layer systems, i.e. systems having three emitting layers, where at least one of these layers comprises at least one compound of the formula (1) and where the three layers exhibit blue, green and orange or red emission (for the basic structure see, for example, WO 05/011013). Emitters which have broadband emission and thus exhibit white emission are likewise suitable for white emission.

In a preferred embodiment of the invention, the compounds of the formulae (1) and (2) to (7) are employed as host material for fluorescent dopants, in particular for blue-fluorescent dopants. In this case, the Ar group is preferably selected from simple or condensed aryl groups, in particular phenyl, ortho-, meta- or para-biphenyl, 1-naphthyl, 2-naphthyl, 2-, 3- or 9-phenanthrenyl or 4- or 5-benz[a]anthracene, which may each be substituted by one or more radicals R1.

A host material in a system comprising host and dopant is taken to mean the component which is present in the higher proportion in the system. In a system comprising one host and a plurality of dopants, the host is taken to mean the component which has the highest proportion in the mixture.

The proportion of the host material of the formulae (1) and (2) to (7) in the emitting layer is between 50.0 and 99.9% by weight, preferably between 80.0 and 99.5% by weight, particularly preferably between 90.0 and 99.0% by weight. Correspondingly, the proportion of the dopant is between 0.01 and 50.0% by weight, preferably between 0.1 and 20.0% by weight, particularly preferably between 0.5 and 15% by weight, very particularly preferably between 1.0 and 10.0% by weight.

Preferred dopants are selected from the class of the monostyrylamines, the distyrylamines, the tristyrylamines, the tetrastyrylamines, the styrylphosphines, the styryl ethers and the arylamines. A monostyrylamine is taken to mean a compound which contains one substituted or unsubstituted styryl group and at least one, preferably aromatic amine. A distyrylamine is taken to mean a compound which contains two substituted or unsubstituted styryl groups and at least one, preferably aromatic amine. A tristyrylamine is taken to mean a compound which contains three substituted or unsubstituted styryl groups and at least one, preferably aromatic amine. A tetrastyrylamine is taken to mean a compound which contains four substituted or unsubstituted styryl groups and at least one, preferably aromatic amine. The styryl groups are particularly preferably stilbenes, which may also be further substituted. Corresponding phosphines and ethers are defined analogously to the amines. For the purposes of this invention, an arylamine or an aromatic amine is taken to mean a compound which contains three substituted or unsubstituted aromatic or heteroaromatic ring systems bonded directly to the nitrogen. At least one of these aromatic or heteroaromatic ring systems is preferably a condensed ring system, preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred dopants are selected from indenofluorenamines or indenofluorenediamines, for example in accordance with WO 06/122630, benzoindenofluorenamines or benzoindenofluorenediamines, for example in accordance with WO 08/006,449, and dibenzoindenofluorenamines or dibenzoindenofluorenediamines, for example in accordance with WO 07/140,847. Examples of dopants from the class of the styrylamines are substituted or unsubstituted tristilbenamines or the dopants described in WO 06/000388, WO 06/058737, WO 06/000389, WO 07/065,549 and WO 07/115,610.

In a further preferred embodiment of the invention, the compounds of the formulae (1) and (2) to (7) are employed as electron-transport material and/or as hole-blocking material. It is preferred here for one or more substituents R1 and/or R2 to contain at least one C=O, P(=O) and/or $SO_2$ unit. It is likewise preferred here for one or more substituents R1 and/or R2 to contain an electron-deficient heterocycle, such as, for example, imidazole, pyrazole, thiazole, benzimidazole, benzothiazole, triazole, oxadiazole, benzothiadiazole, phenanthroline, etc. It is likewise preferred for the Ar group to contain an electron-deficient heterocycle, such as, for example, imidazole, pyrazole, thiazole, benzimidazole, benzothiazole, triazole, oxadiazole, benzothiadiazole, phenanthroline, etc., or for the Ar group to stand for at least one of these heterocycles. Particularly preferred Ar groups, if the compound of the formulae (1) to (7) is intended to be used as electron-transport compound, are the groups of the formulae (9), (10) and (11). It may furthermore be preferred for the compound to be doped with electron-donor compounds.

If the compound of the formulae (1) and (2) to (7) is employed as electron-transport compound, it is preferably employed in an electron-transport layer or electron-injection layer in a fluorescent or phosphorescent electroluminescent device. For the purposes of this invention, an electron-transport layer is taken to mean a layer which is adjacent to an emission layer or a hole-blocking layer on one side and to an electron-injection layer or the cathode on the other side. An electron-injection layer is taken to mean a layer which is adjacent to the cathode on one side and to an emission layer or a hole-blocking layer or an electron-transport layer on the other side.

If the compound of the formulae (1) and (2) to (7) is employed as hole-blocking compound, it is preferably employed in a hole-blocking layer in a fluorescent or phosphorescent electroluminescent device. For the purposes of this invention, a hole-blocking layer is taken to mean a layer which is adjacent to an emission layer on one side and to an electron-transport layer on the other side.

In a further embodiment of the invention, the compounds of the formulae (1) and (2) to (7) are employed as emitting material, in particular in combination with a host material. It is preferred here for one or more substituents R1 and/or R2, in particular one or more substituents R2, to stand for a group of the formula N(Ar1)$_2$.

Preference is furthermore given to an organic electroluminescent device, characterised in that one or more layers are applied by means of a sublimation process, in which the materials are vapour-deposited in vacuum sublimation units at a pressure below $10^{-5}$ mbar, preferably below $10^{-6}$ mbar, particularly preferably below $10^{-7}$ mbar.

Preference is likewise given to an organic electroluminescent device, characterised in that one or more layers are applied by means of the OVPD (organic vapour phase deposition) process or with the aid of carrier-gas sublimation, where the materials are applied at a pressure between $10^{-5}$ mbar and 1 bar.

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds are necessary for this purpose. High solubility can be achieved through suitable substitution of the compounds. Processing and application of the substances in the form of a microemulsion is likewise preferred.

These processes are generally known to the person skilled in the art, and the person skilled in the art can use them for the materials according to the invention without an inventive step.

The compounds according to the invention have increased efficiency and a significantly longer lifetime on use in organic electroluminescent devices, making the organic electroluminescent devices according to the invention particularly well suited to use in high-quality and long-lived displays. This applies, in particular, on use of the materials as host material for blue dopants and/or as electron-transport material. Furthermore, the compounds according to the invention have high thermal stability and a high glass-transition temperature and can be sublimed without decomposition.

The present application text is directed to the use of the compounds according to the invention in relation to OLEDs and the corresponding displays. In spite of this restriction of the description, it is possible for the person skilled in the art, without further inventive step, also to employ the compounds according to the invention in other electronic devices, for example in organic field-effect transistors (O-FETs), organic thin-film transistors (O-TFTs), organic light-emitting transistors (O-LETs), organic integrated circuits (O-ICs), organic solar cells (O-SCs), organic field-quench devices (O-FQDs), light-emitting electrochemical cells (LECs), organic laser diodes (O-lasers) or organic photoreceptors.

The present invention likewise relates to the use of the compounds according to the invention in the corresponding devices and to these devices themselves.

The invention is explained in greater detail by the following examples, without wishing to restrict it thereto. The person skilled in the art will be able to prepare further compounds according to the invention and use them in organic electronic devices without an inventive step.

EXAMPLES

The following syntheses are carried out under a protective-gas atmosphere in dried solvents, unless indicated otherwise. The starting materials can be purchased from ALDRICH.

Example 1

6-(10-Naphthalen-2-ylanthracen-9-yl)phenanthrene a) (E)-2-(4-bromophenyl)-3-(2-nitrophenyl)acrylic acid

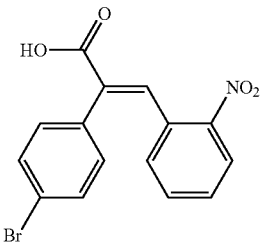 [SMILES: O=C(O)/C(=C/c1ccccc1[N+](=O)[O-])c1ccc(Br)cc1]

64.7 g (0.43 mol) of 2-nitrobenzaldehyde and 105.7 g (0.43 mol) of 4-bromophenylacetic acid sodium salt are dissolved in 500 ml of acetic anhydride and stirred at 80° C. for 2 h. When the reaction is complete, the mixture is extended with 1000 ml of water and 750 ml of EtOH and heated to 110° C., and, after 20 min, the orange solid is filtered off with suction, washed with water and MeOH and dried, giving 107 g (71.8%) of a yellow powder.

b) (E)-2-(4-bromophenyl)-3-(2-aminophenyl)acrylic acid

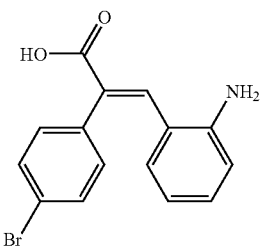

506 g (1.8 mol) of iron (II) sulfate are initially introduced in 475 ml of water and 1000 ml of 25% NH$_4$OH solution and heated to the boil. 79.3 g (228 mmol) of (E)-2-(4-bromophenyl)-3-(2-nitrophenyl)acrylic acid in a mixture of 150 ml of 10% NH$_4$OH solution and 200 ml of THF are added dropwise over the course of 30 min, and the mixture is heated at the boil for a further 30 min. The reaction mixture is filtered hot through Celite, washed with warm 10% NH$_4$OH solution and neutralised using acetic acid, and the resultant solid is filtered off with suction, washed with water and MeOH and dried. Yield of yellow, felt-like crystals: 52 g (72.3%).

c) 6-Bromophenanthrene-9-carboxylic acid

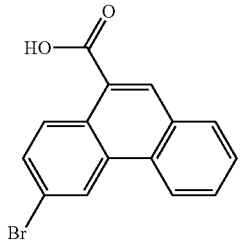 [SMILES: O=C(O)c1cc2ccccc2c2cc(Br)ccc12]

Solution 1: 25.5 g (80 mmol) of (E)-2-(4-bromophenyl)-3-(2-aminophenyl)-acrylic acid are suspended in 440 ml of EtOH, 15.2 ml (128 mmol) of tert-butyl nitrite are added dropwise, then 9 ml of conc. $H_2SO_4$ are added dropwise with ice-cooling, and the mixture is stirred at 5° C. for 1 h. The mixture is extended with 140 ml of water.

Solution 2: A solution of 93.6 g (551 mmol) of calcium hypophosphite in 770 ml of water at 80° C. is added to a solution of sodium carbonate in 550 ml of water at 80° C., the precipitate is filtered off with suction, the filtrate is initially introduced in a second apparatus and brought to an internal temperature of 50° C., and 440 mg (7 mmol) of copper powder are added. Solution 1 is added dropwise to this suspension, and the mixture is stirred vigorously at 50° C. for 3 h. The precipitate is filtered off with suction, washed with water and MeOH, dissolved in toluene and filtered through silica gel.

Yield: 21.8 g (90.4%) of yellow powder.

d) 6-(10-Naphthalen-2-ylanthracen-9-yl)phenanthrene-9-carboxylic acid

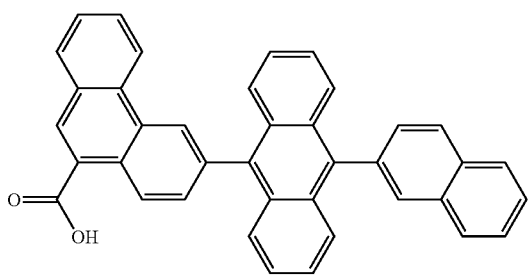 [SMILES: O=C(O)c1cc2ccccc2c2cc(-c3c4ccccc4c(-c4ccc5ccccc5c4)c4ccccc34)ccc12]

51.6 g (148 mmol) of 10-naphth-2-ylanthracen-9-ylboronic acid, 37.2 g (124 mmol) of 6-bromophenanthrene-9-carboxylic acid and 220 ml of 2 M $Na_2CO_3$ solution are suspended in 1 l of toluene and 1 l of EtOH, the suspension is saturated with $N_2$, 2.9 g (3 mmol) of tetrakis(triphenylphosphine)palladium(0) are added, and the mixture is heated at the boil for 2 h. The mixture is poured into 3 l of a mixture of water/MeOH/6 M HCl 1:1:1, and the beige precipitate is filtered off with suction, washed with water, EtOH and toluene and dried. The content of product according to $^1$H-NMR is about 94% with an overall yield of 58 g (90%).

e) 6-(10-Naphthalen-2-ylanthracen-9-yl)phenanthrene

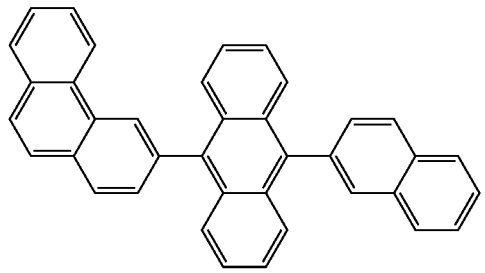 [SMILES: c1ccc2cc(-c3c4ccccc4c(-c4ccc5ccc6ccccc6c5c4)c4ccccc34)ccc2c1]

49 g (94 mmol) of 6-(10-naphth-2-ylanthracen-9-yl)phenanthrene-9-carboxylic acid are suspended in 250 ml of quinoline, the suspension is saturated with $N_2$, 11.8 g (38 mmol) of copper chromite are added, and the mixture is heated at the boil for 8 h. The mixture is subsequently poured into 1 l of MeOH/water, and the black solid is filtered off with suction, washed with MeOH and subjected to Soxhlet extraction with $CHCl_3$. Removal of the solvent leaves a greyish solid, which is recrystallised four times from chlorobenzene and sublimed twice in vacuo (p=1×10$^{-5}$ mbar, T=360° C.). The yield is 32 g (71%) with a purity>99.9%.

Example 2

9-Phenanthren-3-yl-10-phenylanthracene

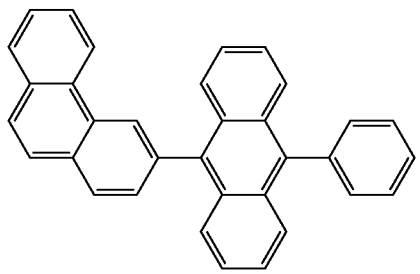 [SMILES: c1ccc(-c2c3ccccc3c(-c3ccc4ccc5ccccc5c4c3)c3ccccc23)cc1]

Starting from 30 g (100 mmol) of 10-phenylanthracene-9-boronic acid and 23.9 g (90 mmol) of 6-bromophenanthrene-9-carboxylic acid, an analogous process to that described under Example 1d) and e) gives a pale-yellow solid (24.4 g, 63%) after recrystallisation four times from chlorobenzene and sublimation at 390° C. (1×10$^{-5}$ mbar).

Example 3

9-Biphenyl-3-yl-10-phenanthren-3-ylanthracene

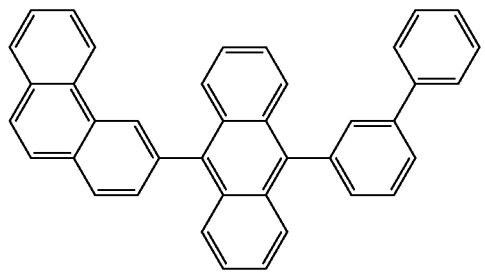 [SMILES: c1ccc(-c2cccc(-c3c4ccccc4c(-c4ccc5ccc6ccccc6c5c4)c4ccccc34)c2)cc1]

Starting from 45 g (100 mmol) of 10-(3-phenyl)phenylanthracene-9-boronic acid and 23.9 g (90 mmol) of 6-bromophenanthrene-9-carboxylic acid, an analogous process to that described under Example 1d) and e) gives a pale-yellow solid (20.5 g, 45%) after recrystallisation four times from NMP and sublimation at 365° C. (1×10$^{-5}$ mbar).

Example 4

2,6-Di-tert-butyl-9,10-bis(phenanthren-3-yl)anthracene

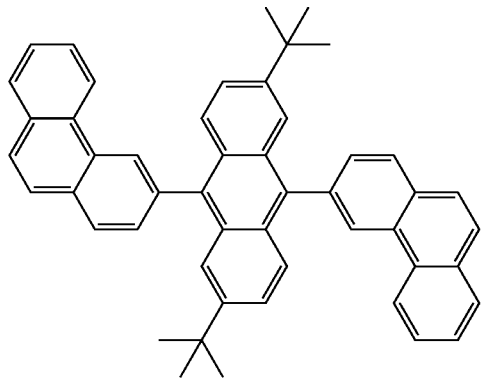 [SMILES: CC(C)(C)c1ccc2c(-c3ccc4ccc5ccccc5c4c3)c3cc(C(C)(C)C)ccc3c(-c3ccc4ccc5ccccc5c4c3)c2c1]

Starting from 18.9 g (50 mmol) of 2,6-di-tert-butylanthracene-9,10-di-boronic acid and 26.6 g (100 mmol) of 6-bromophenanthrene-9-carboxylic acid, an analogous process to that described under Example 1d) and e) gives a pale-yellow solid (23.7 g, 74%) after recrystallisation three times from dioxane and sublimation at 380° C. (1×10$^{-5}$ mbar).

Example 5

2-[4-(10-Phenanthren-3-ylanthracen-9-yl)phenyl]-1-phenyl-1H-benzimidazole a) 6-Anthracen-9-ylphenanthrene-9-carboxylic acid

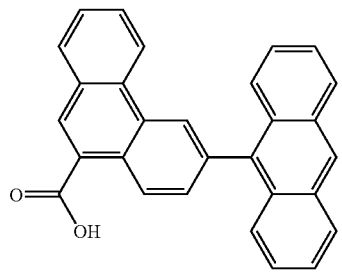 [SMILES: O=C(O)c1cc2ccccc2c2cc(-c3c4ccccc4cc4ccccc34)ccc12]

32.86 g (148 mmol) of anthracene-9-boronic acid, 37.2 g (124 mmol) of 6-bromophenanthrene-9-carboxylic acid and 220 ml of 2 M Na$_2$CO$_3$ solution are suspended in 1 l of toluene and 1 l of EtOH, the mixture is saturated with N$_2$, 2.9 g (3 mmol) of tetrakis(triphenylphosphine)palladium(0) are added, and the mixture is heated at the boil for 2 h. The mixture is poured into 3 l of a mixture of water/MeOH/6 M HCl 1:1:1, and the beige precipitate is filtered off with suction, washed with water, EtOH and toluene and dried. The content of product according to $^1$H-NMR is about 96% with an overall yield of 38.5 g (78%).

b) 9-Phenanthren-3-ylanthracene

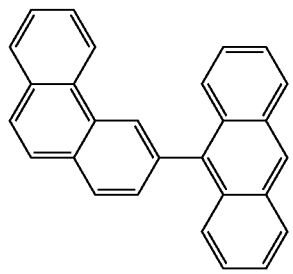 [SMILES: c1ccc2c(-c3ccc4ccc5ccccc5c4c3)c3ccccc3cc2c1]

40 g (94 mmol) of 6-anthracen-9-ylphenanthrene-9-carboxylic acid are suspended in 250 ml of quinoline, the suspension is saturated with N$_2$, 11.8 g (38 mmol) of copper chromite are added, and the mixture is heated at the boil for eight hours. The mixture is subsequently poured into 1 l of MeOH/water, and the black solid is filtered off with suction, washed with MeOH and subjected to Soxhlet extraction with CHCl$_3$. Removal of the solvent leaves a greyish solid, which is recrystallised twice from dioxane. The yield is 30.6 g (92%).

c) 9-Bromo-10-phenanthren-3-ylanthracene

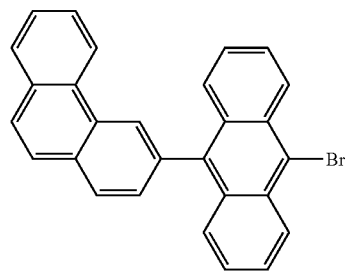 [SMILES: Brc1c2ccccc2c(-c2ccc3ccc4ccccc4c3c2)c2ccccc12]

30 g (80 mmol) of 9-phenanthren-3-ylanthracene are suspended in 300 ml of THF, 14.2 g (80 mmol) of NBS are added, and the mixture is stirred at RT for 2 h with exclusion of light. The solvent is subsequently removed in vacuo, and the residue is boiled in EtOH and recrystallised twice from dioxane, leaving 32.9 g (95%) of bromide as yellow crystals.

d) 2-[4-(10-Phenanthren-3-ylanthracen-9-yl)phenyl]-1-phenyl-1H-benzimidazole

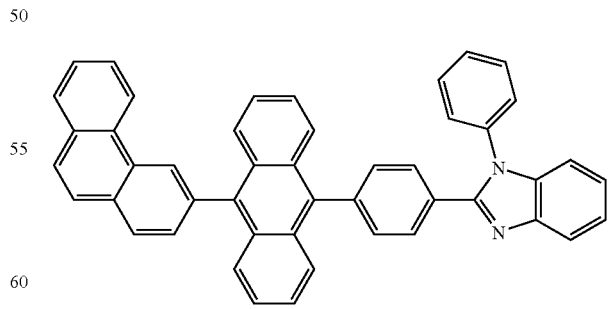

32 g (70 mmol) of 9-bromo-10-phenanthren-3-ylanthracene, 26.3 g (84 mmol) of 4-(1-phenyl-1H-benzimidazol-2-yl)phenylboronic acid and 125 ml of 2 M Na$_2$CO$_3$ solution are suspended in 500 ml of toluene and 500 ml of EtOH, the mixture is saturated with N$_2$, 1.7 g (1.8 mmol) of tetrakis (triphenylphosphine)palladium(0) are added, and the mixture is heated at the boil for 2 h. The mixture is poured into 1.5 l of a mixture of water/MeOH/6 M HCl 1:1:1, and the yellow precipitate is filtered off with suction, washed with water, EtOH and toluene and dried. Subsequent Soxhlet extraction with chloroform, removal of the solvent, recrystallisation three times from toluene and sublimation twice in vacuo ($p=1\times10^{-5}$ mbar, T=385° C.) give 30 g (68%) of a pale-yellow powder having a purity of >99.9% (HPLC).

Example 6

Production of OLEDs

OLEDs are produced by a process which is described in general terms in WO 04/058911 and which is adapted in individual cases to the respective circumstances (for example layer-thickness variation in order to achieve optimum efficiency or colour).

Examples 7 to 17 below show the results for various OLEDs. Glass plates coated with structured ITO (indium tin oxide) form the substrates of the OLEDs. The OLEDs consist of the following layer sequence: substrate/hole-injection layer (HIL1) 60 nm/hole-transport layer (HTM1) 60 nm/emission layer (EML) 30 nm/electron-transport layer (ETM) 20 nm and finally a cathode. The materials are vapour-deposited thermally in a vacuum chamber. The emission layer here always consists of a matrix material (host) and a dopant, which is admixed with the host by co-evaporation. The cathode is formed by a 1 nm thin LiF layer and a 150 nm Al layer deposited on top.

Table 1 shows the chemical structures of the materials used to build up the OLEDs.

These OLEDs are characterised by standard methods; for this purpose, the electroluminescence spectra, the efficiency (measured in cd/A), the power efficiency (measured in lm/W) as a function of the luminance, calculated from current-voltage-luminance characteristic lines (IUL characteristic lines), and the lifetime are determined. The lifetime is defined as the time after which the initial luminance has dropped from 6000 cd/m² to half.

Table 2 shows the results for some OLEDs (Examples 7 to 17). The host materials or electron-transport materials according to the invention used are the compounds of Examples 1 to 4 or 5. The comparative examples used are the host H1 or the electron-transport materials ETM1 and ETM2 in accordance with the prior art.

As can clearly be seen from the results in Table 2, organic electroluminescent devices comprising the compounds according to the invention have a longer lifetime and better efficiency than organic electroluminescent devices in accordance with the prior art.

TABLE 1

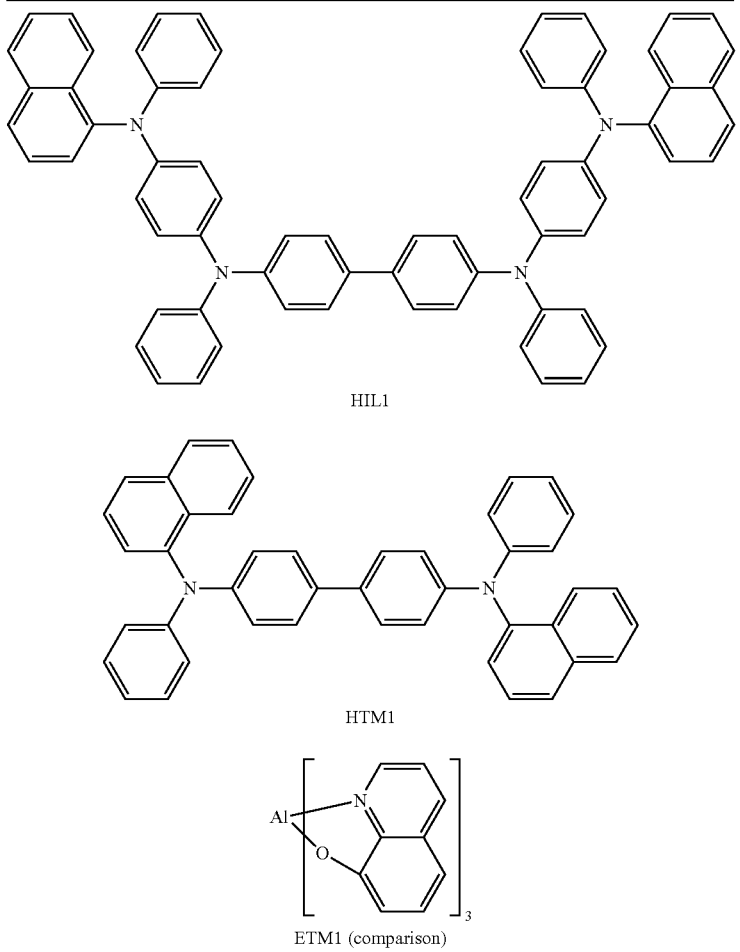

TABLE 1-continued
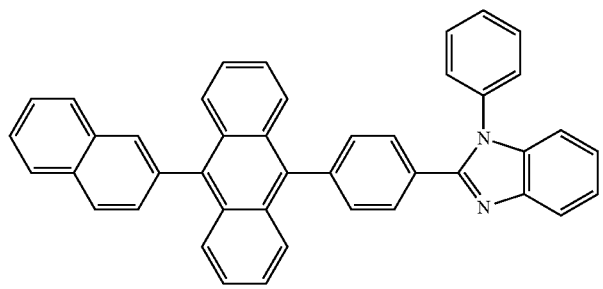 [SMILES: c1ccc(-n2c(-c3ccc(-c4c5ccccc5c(-c5ccc6ccccc6c5)c5ccccc45)cc3)nc3ccccc32)cc1]
ETM2
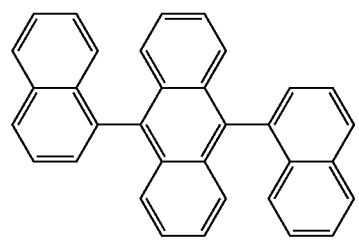 [SMILES: c1ccc2c(-c3c4ccccc4c(-c4cccc5ccccc45)c4ccccc34)cccc2c1]
H1 (comparison)
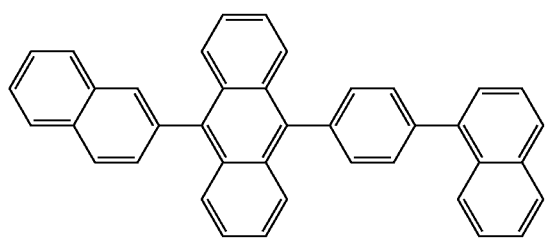 [SMILES: c1ccc2cc(-c3c4ccccc4c(-c4ccc(-c5cccc6ccccc56)cc4)c4ccccc34)ccc2c1]
H2 (comparison)
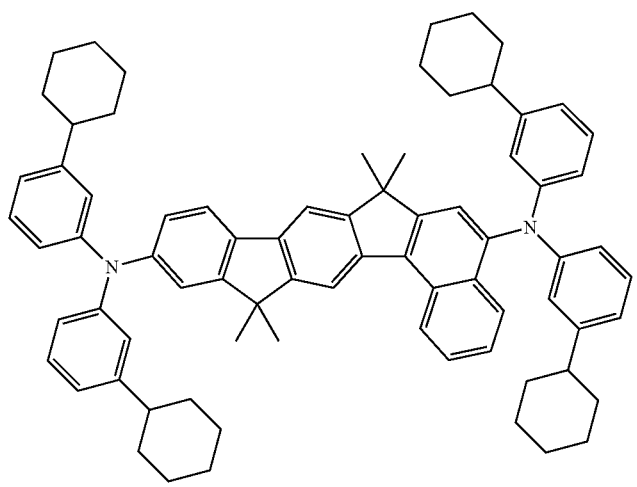 [SMILES: CC1(C)c2cc(N(c3cccc(C4CCCCC4)c3)c3cccc(C4CCCCC4)c3)ccc2-c2cc3c(cc21)-c1c(cc(N(c2cccc(C4CCCCC4)c2)c2cccc(C4CCCCC4)c2)c2ccccc12)C3(C)C]
D1

TABLE 1-continued
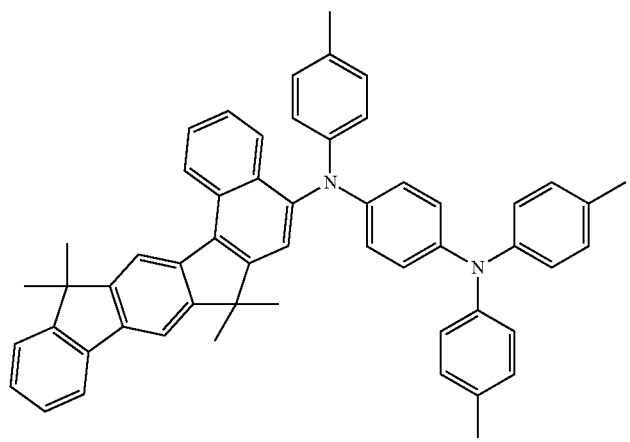 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]
D2
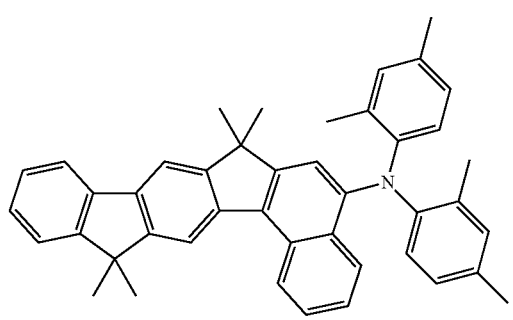 [SMILES: Cc1ccc(N(c2ccc(C)cc2C)c2cc3c(c4ccccc24)-c2cc4c(cc2C3(C)C)-c2ccccc2C4(C)C)c(C)c1]
D3
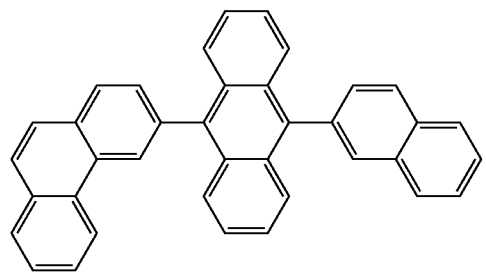 [SMILES: c1ccc2cc(-c3c4ccccc4c(-c4ccc5ccc6ccccc6c5c4)c4ccccc34)ccc2c1]
Ex. 1
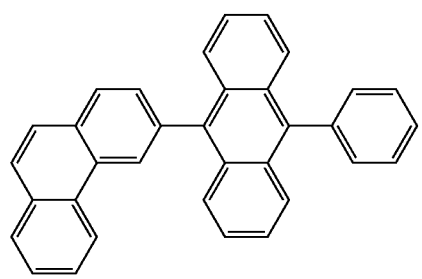 [SMILES: c1ccc(-c2c3ccccc3c(-c3ccc4ccc5ccccc5c4c3)c3ccccc23)cc1]
Ex. 2

TABLE 1-continued
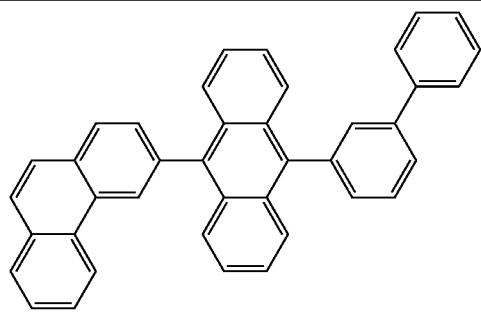
Ex. 3
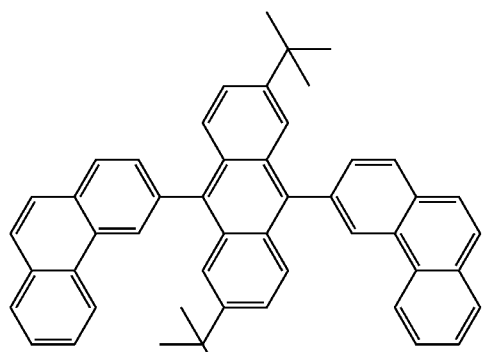
Ex. 4
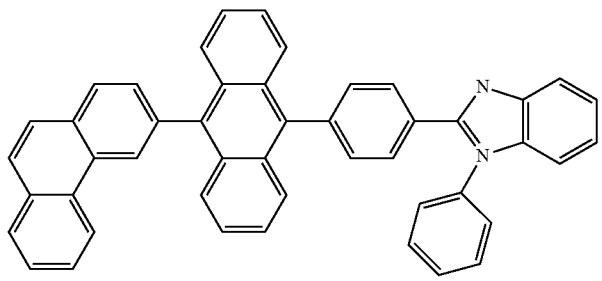
Ex. 5
TABLE 2
| Example | EML | ETM | Max. efficiency (cd/A) | Voltage (V) at 1000 cd/m² | CIE | Lifetime at 6000 cd/m² (h) |
|---|---|---|---|---|---|---|
| 7 (comparison) | H1 +5% of D1 | ETM1 | 6.8 | 5.6 | x = 0.14/ y = 0.18 | 390 |
| 8 (comparison) | H2 +5% of D1 | ETM1 | 7.2 | 5.5 | x = 0.15/ y = 0.19 | 420 |
| 9 (comparison) | H2 +5% of D1 | ETM2 | 7.8 | 5.3 | x = 0.15/y = 0.19 | 350 |
| 10 | Ex. 1 + 5% of D1 | ETM1 | 7.4 | 5.7 | x = 0.15/y = 0.19 | 440 |
| 11 | Ex. 2 + 5% of D1 | ETM1 | 7.3 | 5.3 | x = 0.15/y = 0.19 | 400 |
| 12 | Ex. 3 + 5% of D1 | ETM1 | 7.5 | 5.7 | x = 0.15/y = 0.19 | 480 |
| 13 | Ex. 1 + 5% of D1 | Ex. 5 | 8.1 | 5.6 | x = 0.16/y = 0.18 | 390 |
| 14 | Ex. 2 + 5% of D1 | Ex. 5 | 8.4 | 5.2 | x = 0.16/y = 0.19 | 370 |
| 15 | Ex. 3 + 5% of D1 | Ex. 5 | 8.5 | 5.7 | x = 0.15/y = 0.20 | 420 |
| 16 | Ex. 4 + 5% of D2 | ETM1 | 20 | 5.8 | x = 0.29/y = 0.60 | 3500 |
| 17 | Ex. 4 + 5% of D2 | Ex. 5 | 24 | 5.9 | x = 0.29/y = 0.61 | 4200 |
| 18 | Ex. 1 + 5% of D3 | ETM1 | 6.1 | 5.6 | x = 0.15/y = 0.15 | 390 |

The invention claimed is:
1. A compound of the formula (1)

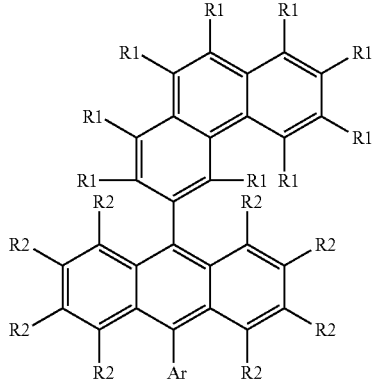

formula (1)

where the following applies to the symbols used:
Ar is selected from phenyl, 2- phenanthrenyl, 3- phenanthrenyl, 9-phenanthrenyl, para-phenylene-1-naphthyl, para-phenylene-2-naphthyl, 2-fluorenyl or 2-spirobifluorenyl, which is optionally substituted by one or more radicals R1, or the Ar group is selected from the formulae (8), (9), (10) and (11):

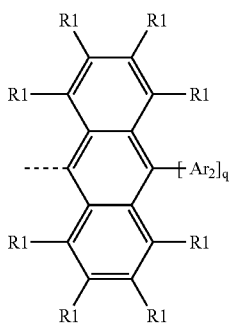

formula (8)

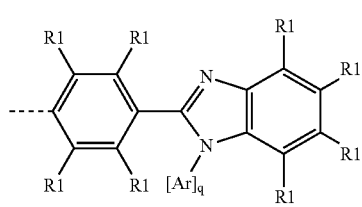

formula (9)

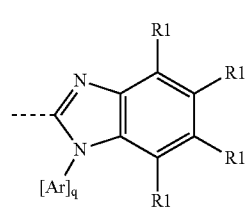

formula (10)

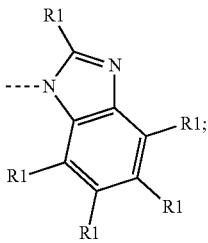

formula (11)

Ar2 is an aryl or heteroaryl group having 5 to 16 aromatic ring atoms which is optionally substituted by one or more radicals R1;
q is 1;
R1 is, identically or differently on each occurrence, H, D, F, Cl, Br, I, CHO, N(Ar1)$_2$, C(=O)Ar1, P(Ar1)$_2$, P(=O)(Ar1)$_2$, S(=O)Ar1, S(=O)$_2$Ar1, CR3=CR3Ar1, CN, NO$_2$, Si(R3)$_3$, B(OAr1)$_2$, B(OR3)$_2$, OSO$_2$R3, OH, a straight-chain alkyl, alkoxy or thioalkoxy group having 1 to 40 C atoms or a branched or cyclic alkyl, alkoxy or thioalkoxy group having 3 to 40 C atoms, which is optionally substituted by one or more radicals R3, where one or more non-adjacent CH$_2$ groups is optionally replaced by R3C=CR3, C≡C, Si(R3)$_2$, Ge(R3)$_2$, Sn(R3)$_2$, C=O, C=S, C=Se, C=NR3, P(=O)(R3), SO, SO$_2$, NR3, O, S or CONR3 and where one or more H atoms is optionally replaced by F, Cl, Br, I, CN or NO$_2$, or an aromatic or heteroaromatic ring system having 5 to 60 aromatic ring atoms, which are each optionally substituted by one or more non-aromatic radicals R1, or an aryloxy or heteroaryloxy group having 5 to 60 aromatic ring atoms, which is optionally substituted by one or more non-aromatic radicals R1;
R2 is, identically or differently on each occurrence, R1;
Ar1 is, identically or differently on each occurrence, an aromatic or heteroaromatic ring system having 5 to 30 aromatic ring atoms, which is optionally substituted by one or more non-aromatic radicals R3; two radicals Ar1 which are bonded to the same nitrogen or phosphorus atom may optionally be linked to one another by a single bond or a bridge selected from B(R3), C(R3)$_2$, Si(R3)$_2$, C=O, C=NR3, C=C(R3)$_2$, O, S, S=O, SO$_2$, N(R3), P(R3) and P(=O)R3;
R3 is on each occurrence, identically or differently, H or an aliphatic, aromatic and/or heteroaromatic hydrocarbon radical having 1 to 20 C atoms, in which, in addition, one or more H atoms is optionally replaced by F;
with the provisos that R2 in positions 2, 3, 6, and 7 of anthracene is not N(Ar1)$_2$ or an aromatic or heteroaromatic ring system having 5 to 60 aromatic ring atoms and Ar is not ortho-biphenyl, meta-biphenyl, or para-biphenyl.

2. The compound according to claim 1, wherein the symbols R1 and R2, identically or differently on each occurrence, stand for H, F, N(Ar1)$_2$, C(=O)Ar1, P(Ar1)$_2$, P(=O)(Ar1)$_2$, S(=O)Ar1, S(=O)$_2$Ar1, CR3=CR3Ar1, Si(R3)$_3$, B(OAr1)$_2$, B(OR3)$_2$, a straight-chain alkyl or alkoxy group having 1 to 20 C atoms or a branched or cyclic alkyl or alkoxy group having 3 to 20 C atoms, which is optionally substituted by one or more radicals R3, where one or more non-adjacent CH$_2$ groups is optionally replaced by R3C=CR3, C≡C, Si(R3)$_2$, C=O, P(=O)(R3), SO, SO$_2$, NR3, O or S and where one or more H atoms is optionally replaced by F, or an aromatic or heteroaromatic ring system having 5 to 40 aromatic ring atoms, which are each optionally substituted by one or more non-aromatic radicals R1.

3. A process for the preparation of the compound according to claim 1, which comprises substituting 9-aryl-substituted anthracene in the 10-position by a reactive leaving group, and coupling the 9-aryl-substituted anthracene to a phenanthrene derivative which is functionalised in the 3-position, where both the phenanthrene and also the anthracene, benzanthracene or tetracene are optionally substituted by one or more substituents R1.

4. The process as claimed in claim 3, wherein the reactive leaving group is chlorine, bromine, iodine, triflate, tosylate, boronic acid or boronic acid ester, or a corresponding benz[a]anthracene or tetracene.

5. An electronic device which comprises at least one compound according to claim 1.

6. The electronic device according to claim 5, wherein the device is selected from the group consisting of an organic electroluminescent device (OLED), organic field-effect transistor (O-FET), organic thin-film transistor (O-TFT), organic light-emitting transistor (O-LET), organic integrated circuit (O-IC), organic solar cell (O-SC), organic field-quench device (O-FQD), light-emitting electrochemical cell (LEC), organic laser diode (O-laser) and organic photoreceptor.

7. An organic electroluminescent device comprising anode, cathode and at least one emitting layer, wherein at least one organic layer, which may be an emitting layer or another layer, comprises at least one compound according to claim 1.

8. The organic electroluminescent device according to claim 7, wherein the compound of formula (1) is employed as a host material for fluorescent dopants.

9. The organic electroluminescent device according to claim 8, wherein the fluorescent dopants comprise compounds which are selected from the group consisting of monostyrylamine, distyrylamine, tristyrylamine, tetrastyrylamine, styrylphosphine, styryl ether, arylamine, indenofluorenamine, indenofluorenediamine, benzoindenofluorenamine, benzoindenofluorenediamine, dibenzoindenfluorenamine and dibenzoindenfluorenediamine.

10. The organic electroluminescent device according to claim 9, wherein the compound of the formula (1) is employed as electron-transport material or as hole-blocking material in a fluorescent or phosphorescent device.

11. A compound selected from the group consisting of

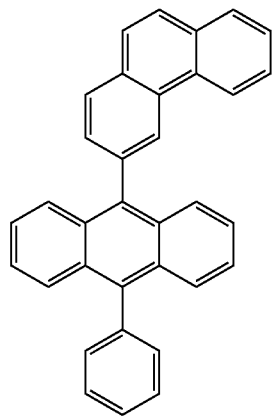

(1)

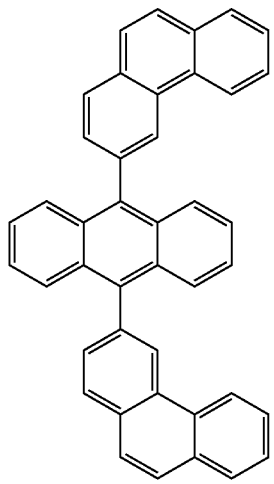

(4)

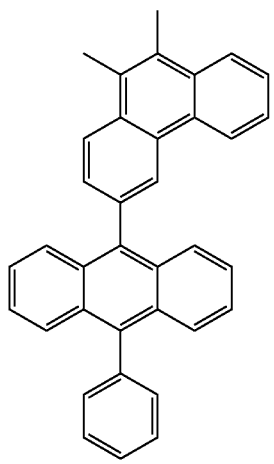

(5)

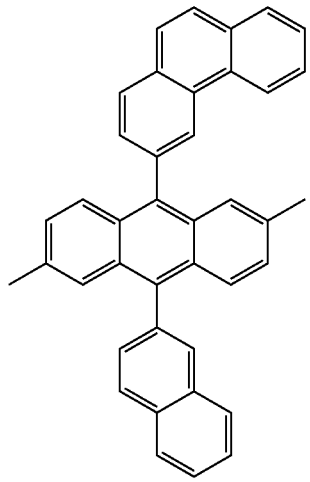

(6)

(7)
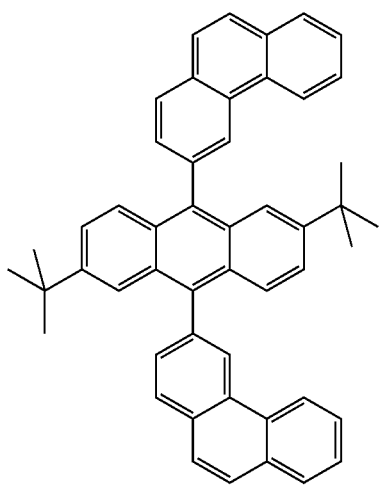
(8)
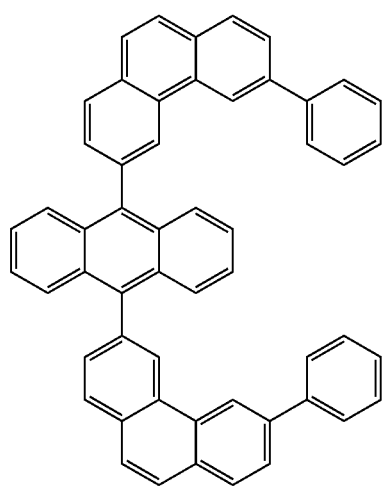
(9)
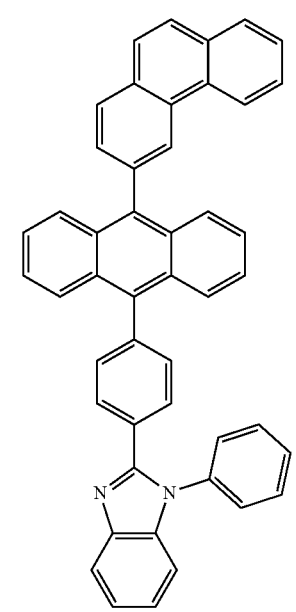
(10)
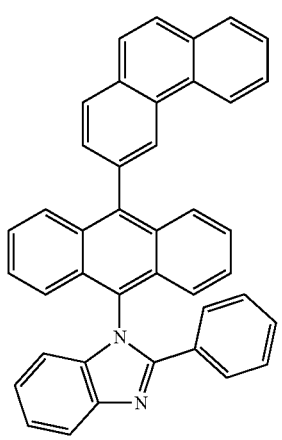
(15)
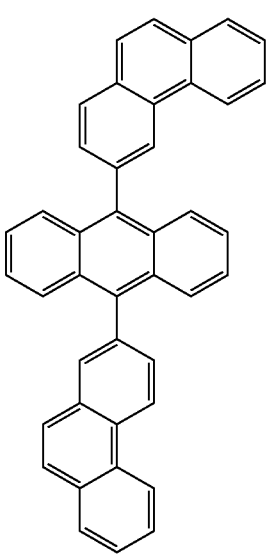
(16)
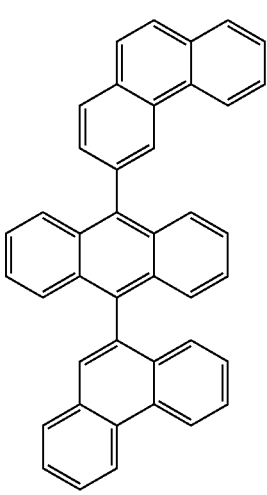

(17)
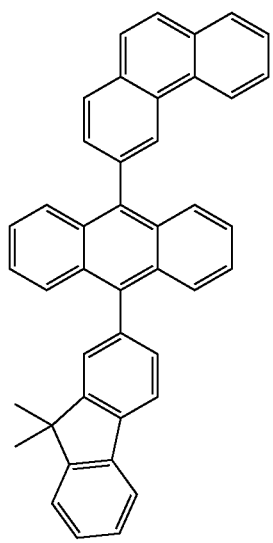
(95)
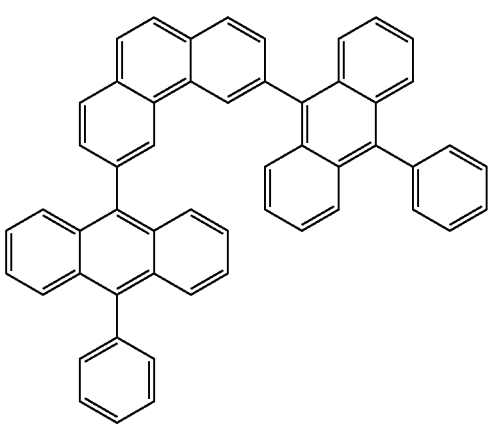
(18)
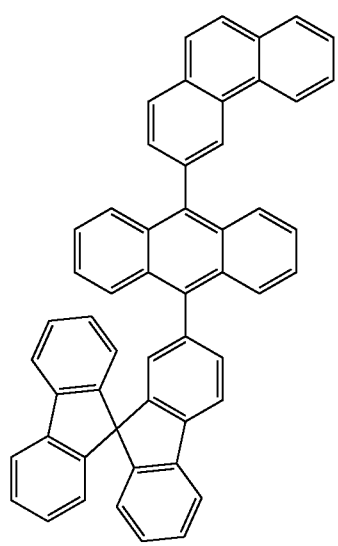
(97)
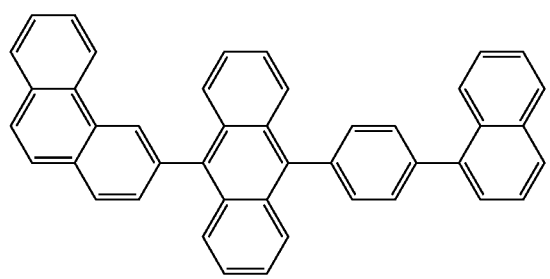
(90)
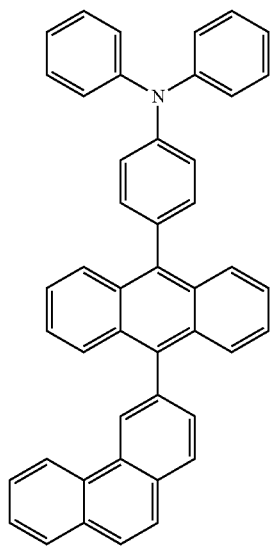
(101)
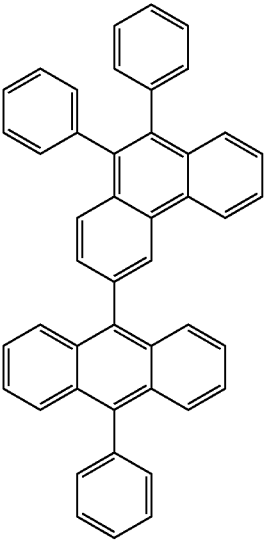

(104)
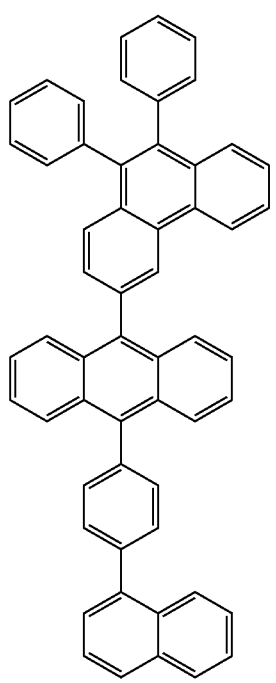
(106)
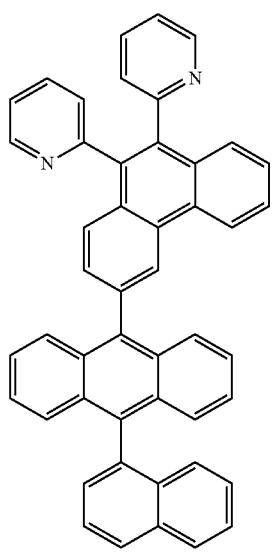
(111)
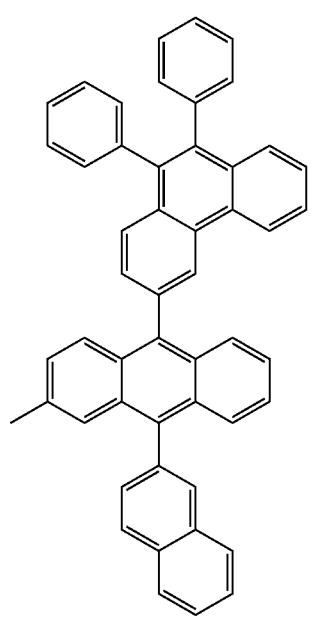
(112)
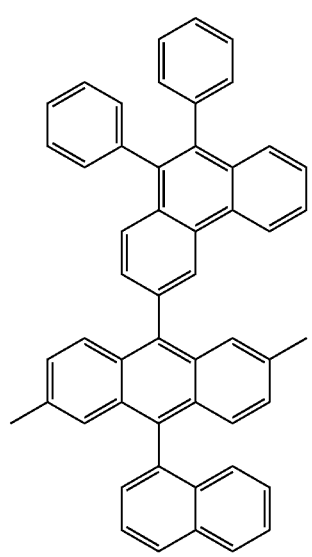

(121)

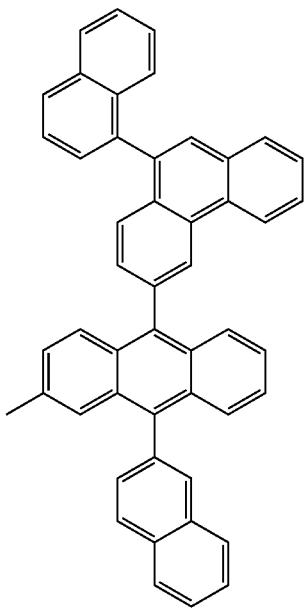

and (122)

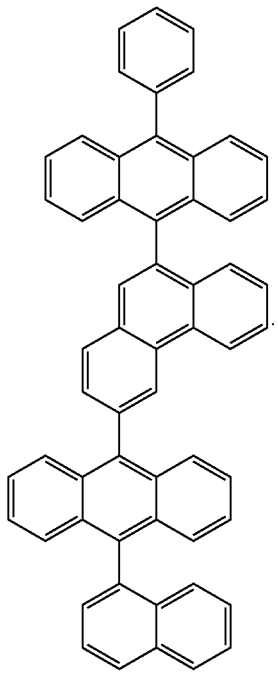

12. The compound according to claim 11, wherein the compound is of the formula (1) or (3).

13. The compound according to claim 1, wherein the compound of the formula (1) is a compound of the formula (2):

formula (2)

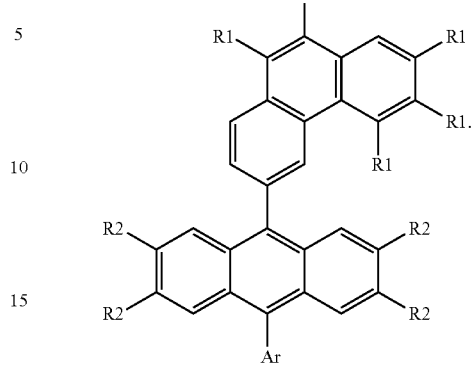

14. The compound according to claim 1, wherein formula (1) is:

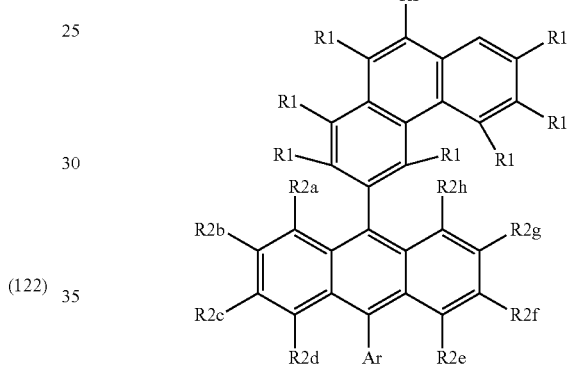

wherein

R2a, R2d, R2e, and R2h are, identically or differently on each occurrence, H, D, F, Cl, Br, I, CHO, N(Ar1)$_2$, C(=O)Ar1, P(Ar1)$_2$, P(=O)(Ar1)$_2$, S(=O)Ar1, S(=O)$_2$Ar1, CR3=CR3Ar1, CN, NO$_2$, Si(R3)$_3$, B(OAr1)$_2$, B(OR3)$_2$, OSO$_2$R3, OH, a straight-chain alkyl, alkoxy or thioalkoxy group having 1 to 40 C atoms or a branched or cyclic alkyl, alkoxy or thioalkoxy group having 3 to 40 C atoms, which is optionally substituted by one or more radicals R3, where one or more non-adjacent CH$_2$ groups is optionally replaced by R3C=CR3, C≡C, Si(R3)$_2$, Ge(R3)$_2$, Sn(R3)$_2$, C=O, C=S, C=Se, C=NR3, P(=O)(R3), SO, SO$_2$, NR3, O, S or CONR3 and where one or more H atoms is optionally replaced by F, Cl, Br, I, CN or NO$_2$, or an aromatic or heteroaromatic ring system having 5 to 60 aromatic ring atoms, which are each optionally substituted by one or more non-aromatic radicals R1, or an aryloxy or heteroaryloxy group having 5 to 60 aromatic ring atoms, which is optionally substituted by one or more non-aromatic radicals R1; and R2b, R2c, R2f, and R2g are, identically or differently on each occurrence, H, D, F, Cl, Br, I, CHO, C(=O)Ar1, P(Ar1)$_2$, P(=O)(Ar1)$_2$, S(=O)Ar1, S(=O)$_2$Ar1, CR3=CR3Ar1, CN, NO₂, Si(R3)₃, B(OAr1)₂, B(OR3)₂, OSO₂R3, OH, a straight-chain alkyl, alkoxy or thioalkoxy group having 1 to 40 C atoms or a branched or cyclic alkyl, alkoxy or thioalkoxy group having 3 to 40 C atoms, which is optionally substituted by one or more radicals R3, where one or more non-adjacent CH₂ groups is optionally replaced by R3C=CR3, C≡C, Si(R3)₂, Ge(R3)₂, Sn(R3)₂, C=O, C=S, C=Se, C=NR3, P(=O)(R3), SO, SO₂, NR3, O, S or CONR3 and where one or more H atoms is optionally replaced by F, Cl, Br, I, CN or NO₂.

15. The compound according to claim 1, wherein R2 is identically or differently on each occurrence, H, D, F, Cl, Br, I, CHO, C(=O)Ar1, P(Ar1)₂, P(=O)(Ar1)₂, S(=O)Ar1, S(=O)₂Ar1, CR3=CR3Ar1, CN, NO₂, Si(R3)₃, B(OAr1)₂, B(OR3)₂, OSO₂R3, OH, a straight-chain alkyl, alkoxy or thioalkoxy group having 1 to 40 C atoms or a branched or cyclic alkyl, alkoxy or thioalkoxy group having 3 to 40 C atoms, which is optionally substituted by one or more radicals R3, where one or more non-adjacent CH₂ groups is optionally replaced by R3C=CR3, C≡C, Si(R3)₂, Ge(R3)₂, Sn(R3)₂, C=O, C=S, C=Se, C=NR3, P(=O)(R3), SO, SO₂, NR3, O, S or CONR3 and where one or more H atoms is optionally replaced by F, Cl, Br, I, CN or NO₂.

16. A compound of the formula (1)

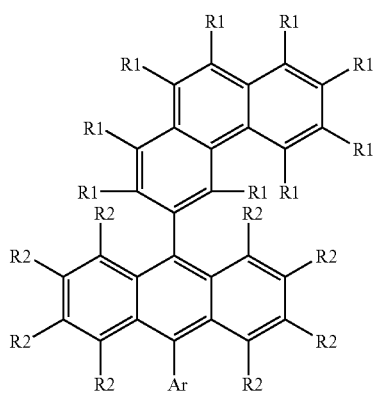

formula (1)

where the following applies to the symbols used:

Ar is selected from phenyl which is optionally substituted by one or more radicals R1, or the Ar group is selected from the formulae (8), (9), (10) and (11):

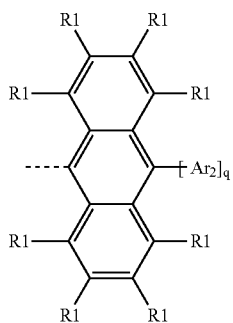

formula (8)

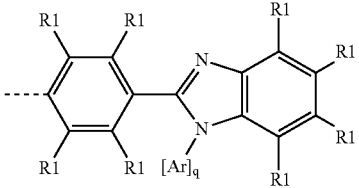

formula (9)

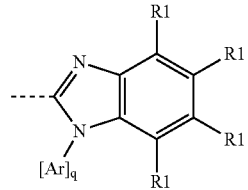

formula (10)

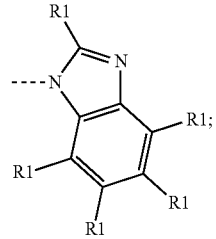

formula (11)

Ar2 is phenyl, 1-naphthyl, 2-naphthyl, 9-anthryl, chrysenyl, 1-pyrenyl, 2-pyrenyl, 2-phenanthrenyl, 3-phenanthrenyl, 9-phenanthrenyl, 2-benzimidazole or fluoranthenyl, which is optionally substituted by one or more radicals R1;

q is 1;

R1 is, identically or differently on each occurrence, H, D, F, Cl, Br, I, CHO, N(Ar1)₂, C(=O)Ar1, P(Ar1)₂, P(=O)(Ar1)₂, S(=O)Ar1, S(=O)₂Ar1, CR3=CR3Ar1, CN, NO₂, Si(R3)₃, B(OAr1)₂, B(OR3)₂, OSO₂R3, OH, a straight-chain alkyl, alkoxy or thioalkoxy group having 1 to 40 C atoms or a branched or cyclic alkyl, alkoxy or thioalkoxy group having 3 to 40 C atoms, which is optionally substituted by one or more radicals R3, where one or more non-adjacent CH₂ groups is optionally replaced by R3C=CR3, C≡C, Si(R3)₂, Ge(R3)₂, Sn(R3)₂, C=O, C=S, C=Se, C=NR3, P(=O)(R3), SO, SO₂, NR3, O, S or CONR3 and where one or more H atoms is optionally replaced by F, Cl, Br, I, CN or NO₂, or an aromatic or heteroaromatic ring system having 5 to 60 aromatic ring atoms, which are each optionally substituted by one or more non-aromatic radicals R1, or an aryloxy or heteroaryloxy group having 5 to 60 aromatic ring atoms, which is optionally substituted by one or more non-aromatic radicals R1;

R2 is, identically or differently on each occurrence, R1;

Ar1 is, identically or differently on each occurrence, an aromatic or heteroaromatic ring system having 5 to 30 aromatic ring atoms, which is optionally substituted by one or more non-aromatic radicals R3; two radicals Ar1 which are bonded to the same nitrogen or phosphorus atom may optionally be linked to one another by a single bond or a bridge selected from B(R3), C(R3)₂, Si(R3)₂, C=O, C=NR3, C=C(R3)₂, O, S, S=O, SO₂, N(R3), P(R3) and P(=O)R3;

R3 is on each occurrence, identically or differently, H or an aliphatic, aromatic and/or heteroaromatic hydrocarbon radical having 1 to 20 C atoms, in which, in addition, one or more H atoms is optionally replaced by F;

with the provisos that R2 in positions 2, 3, 6, and 7 of anthracene is not $N(Ar1)_2$ or an aromatic or heteroaromatic ring system having 5 to 60 aromatic ring atoms and Ar is not ortho-biphenyl, meta-biphenyl, or para-biphenyl.

17. The compound according to claim 1, wherein Ar2 is phenyl, 1-naphthyl, 2-naphthyl, 9-anthryl, chrysenyl, 1-pyrenyl, 2-pyrenyl, 2-phenanthrenyl, 3-phenanthrenyl, 9-phenanthrenyl, 2-benzimidazole or fluoranthenyl, which is optionally substituted by one or more radicals R1.

* * * * *